United States Patent [19]

Heller

[11] Patent Number: 5,849,489
[45] Date of Patent: Dec. 15, 1998

[54] HYBRIDIZATION OF POLYNUCLEOTIDES CONJUGATED WITH CHROMOPHORES AND FLUOROPHORES TO GENERATE DONOR-TO-DONOR ENERGY TRANSFER SYSTEM

[75] Inventor: Michael J. Heller, Encinitas, Calif.

[73] Assignee: Nanogen, Inc., San Diego, Calif.

[21] Appl. No.: 703,601

[22] Filed: Aug. 23, 1996

Related U.S. Application Data

[63] Continuation of Ser. No. 232,233, filed as PCT/US92/09827 Nov. 6, 1992, Pat. No. 5,565,322, which is a continuation-in-part of Ser. No. 250,951, May 27, 1994, Pat. No. 5,532,129, which is a continuation of Ser. No. 790,262, Nov. 7, 1991, abandoned.

[51] Int. Cl.$^6$ .............................. C12Q 1/68; C07H 21/04; G01N 27/00; G01N 37/00
[52] U.S. Cl. ............................... 435/6; 435/56; 435/800; 536/24.3; 422/82.01; 422/82.02; 422/82.08
[58] Field of Search .................................. 435/6, 56, 800; 536/24.3; 422/82.01, 82.02, 82.08

[56] References Cited

U.S. PATENT DOCUMENTS

| | | | |
|---|---|---|---|
| 4,822,746 | 4/1989 | Walt | 436/528 |
| 4,868,103 | 9/1989 | Stavrianopoulos et al. | 435/5 |
| 4,996,143 | 2/1991 | Heller | 435/6 |
| 5,237,515 | 8/1993 | Herron et al. | 364/498 |
| 5,565,322 | 10/1996 | Heller | 435/6 |

FOREIGN PATENT DOCUMENTS 0 229 943   7/1987   European Pat. Off. .

OTHER PUBLICATIONS

Kornberg, Arthur, "DNA Synthesis", 1974.
Cardullo et al., *Proc. Natl. Acad. Sci. USA*, 85:8790–8794 (1988).
Garner et al., *Anal. Chem.*, 62:2193–2198 (1990).
Haddon et al., *Proc. Natl. Acad. Sci. USA*, 92: 1874–1878 (1985).
Heller et al., in "Rapid Detection and Infection of Infectious Diseases", Kingsbury et al., eds, Acad Pr, NY, pp. 245–256 (1985).
Hopfield et al., *Science*, 241:817–820 (1988).
Keller et al., in "DNA Probes", pp. 104–108,Stockton Press, N.Y. (1989).
McAlear et al., in "Molecular Electronic Devices II", pp. 623–633, Carter, et al., Marcel Dekker, Inc., N.Y. (1987).
Morrison et al., *Anal. Biochem.*, 183–231–244 (1989).
Robinson et al., *Protein Eng.*, 1:295–300 (1987).
Glazer, et al., *Emerging Techniques: Physofluor probes*, Trends in Biochemical Sciences, vol. 9, No. 10, pp. 423 (1984).
Tyagi et al., *Molecular Beacons: Probes that Fluoresce upon Hybridization*, Nature Biotechnology, vol. 14 (Mar., 1996).

*Primary Examiner*—W. Gary Jones
*Assistant Examiner*—Jeffrey Fredman
*Attorney, Agent, or Firm*—Lyon & Lyon LLP

[57] ABSTRACT

The present invention contemplates chromophore-containing polynucleotides having at least two donor chromophores operatively linked to the polynucleotide by linker arms, such that the chromophores are positioned by linkage along the length of the polynucleotide at a donor—donor transfer distance, and at least one fluorescing acceptor chromophore operatively linked to the polynucleotide by a linker arm, such that the fluorescing acceptor chromophore is positioned by linkage at a donor-acceptor transfer distance from at least one of the donor chromophores, to form a photonic structure for collecting photonic energy and transferring the energy to an acceptor chromophore, and methods using the photonic structures.

23 Claims, 4 Drawing Sheets

5,849,489

HYBRIDIZATION OF POLYNUCLEOTIDES CONJUGATED WITH CHROMOPHORES AND FLUOROPHORES TO GENERATE DONOR-TO-DONOR ENERGY TRANSFER SYSTEM

This is a continuation of U.S. application Ser. No. 8/232,233, filed on May 5, 1994, now U.S. Pat. No. 5,565,322, which was filed under 35 U.S.C. §371 based on International Application PCT/US92/09827, filed Nov. 6, 1992, which in turn is a continuation-in-part of U.S. application Ser. No. 250,951, filed May 27, 1994, now U.S. Pat. No. 5,532,129, which in turn is a continuation of U.S. application Ser. No. 07/790,262, filed Nov. 7, 1991, now abandoned. Each of the above-identified patents and applications is expressly incorporated herein by reference.

TECHNICAL FIELD

This invention relates to design and synthesis of modified synthetic nucleic acid polymers/oligomers with directly incorporated electronic/photonic transfer properties. In particular, it relates to the property of extended directional non-radiative energy transfer. These unique components can be programmed to self-assemble and organize into larger more complex structures. The directly incorporated electronic/photonic functional properties allow connections and novel mechanisms to be formed within the organized structures. The combination of the properties allows ultimately for the creation of useful photonic and photovoltaic devices, DNA bio-sensors, and DNA diagnostic assay systems.

BACKGROUND OF THE INVENTION

The fields of molecular electronics/photonics and nanotechnology offer immense technological promise for the future. Nanotechnology is defined as a projected technology based on a generalized ability to build objects to complex atomic specifications. Drexler, *Proc. Natl. Acad. Sci USA*, 78:5275–5278, (1981). Nanotechnology means an atom-by-atom or molecule-by-molecule control for organizing and building complex structures all the way to the macroscopic level. Nanotechnology is a bottom-up approach, in contrast to a top-down strategy like present lithographic techniques used in the semiconductor and integrated circuit industries. The success of nanotechnology will be based on the development of programmable self-assembling molecular units and molecular level machine tools, so-called assemblers, which will enable the construction of a wide range of molecular structures and devices. Drexler, in "Engines of Creation," Doubleday Publishing Co., New York, N.Y. (1986). Thus, one of the first and most important goals in nanotechnology is the development of programmable self-assembling molecular construction units.

Present molecular electronic/photonic technology includes numerous efforts from diverse fields of scientists and engineers. Carter, ed. in "Molecular Electronic Devices II," Marcel Dekker, Inc, New York, N.Y. (1987). Those fields include organic polymer based rectifiers, Metzger et al., in "Molecular Electronic Devices II," Carter, ed., Marcel Dekker, New York, N.Y., pp. 5–25 (1987), conducting conjugated polymers, MacDiarmid et al., *Synthetic Metals*, 18:285 (1987), electronic properties of organic thin films or Langmuir-Blogett films, Watanabe et al., *Synthetic Metals*, 28:C473 (1989), molecular shift registers based on electron transfer, Hopfield et al., *Science*, 241:817 (1988), and a self-assembly system based on synthetically modified lipids which form a variety of different "tubular" microstructures. Singh et al., in "Applied Bioactive Polymeric Materials," Plenum Press, New York, N.Y., pp. 239–249 (1988). Molecular optical or photonic devices based on conjugated organic polymers, Baker et al., *Synthetic Metals*, 28:D639 (1989), and nonlinear organic materials have also been described. Potember et al., *Proc. Annual Conf. IEEE in Medicine and Biology*, Part 4/6:1302–1303 (1989).

However, none of the cited references describe a sophisticated or programmable level of self-organization or self-assembly. Typically the actual molecular component which carries out the electronic and/or photonic mechanism is a natural biological protein or other molecule. Akaike et al., *Proc. Annual Conf. IEEE in Medicine and Biology*, Part 4/6:1337–1338 (1989). There are presently no examples of a totally synthetic programmable self-assembling molecule which produces an efficient electronic or photonic structure, mechanism or device.

Progress in understanding self-assembly in biological systems is relevant to nanotechnology. Drexler, *Proc. Natl. Acad. Sci USA*, 78:5275–5278 (1981). Drexler, in "Engines of Creation," Doubleday Publishing Co., New York, N.Y. (1986). Areas of significant progress include the organization of the light harvesting photosynthetic systems, the energy transducing electron transport systems, the visual process, nerve conduction and the structure and function of the protein components which make up these systems. The so called bio-chips described the use of synthetically or biologically modified proteins to construct molecular electronic devices. Haddon et al., *Proc. Natl. Acad. Sci. USA*, 82:1874–1878 (1985). (McAlear et al., in "Molecular Electronic Devices II," Carter ed., Marcel Dekker, Inc., New York N.Y., pp. 623–633 (1987). Some work on synthetic proteins (polypeptides) has been carried out with the objective of developing conducting networks. McAlear et al., in "Molecular Electronic Devices," Carter ed., Marcel Dekker, New York, N.Y., pp. 175–180 (1982). Other workers have speculated that nucleic acid based bio-chips may be more promising. Robinson et al., "The Design of a Biochip: a Self-Assembling Molecular-Scale Memory Device," *Protein Engineering*, 1:295–300 (1987).

Great strides have also been made in our understanding of the structure and function of the nucleic acids, deoxyribonucleic acid or DNA, Watson, et al., in "Molecular Biology of the Gene," Vol. 1, Benjamin Publishing Co., Menlo Park, Calif. (1987), which is the carrier of genetic information in all living organisms. In DNA, information is encoded in the linear sequence of nucleotides by their base units adenine, guanine, cytosine, and thymidine (A, G, C, and T). Single strands of DNA (or polynucleotides) have the unique property of recognizing and binding, by hybridization, to their complementary sequence to form a double stranded nucleic acid duplex structure. This is possible because of the inherent base-pairing properties of the nucleic acids; A recognizes T, and G recognizes C. This property leads to a very high degree of specificity since any given polynucleotide sequence will hybridize only to its exact complementary sequence.

In addition to the molecular biology of nucleic acids, great progress has also been made in the area of the chemical synthesis of nucleic acids (16). This technology has developed so automated instruments can now efficiently synthesize sequences over 100 nucleotides in length, at synthesis rates of 15 nucleotides per hour. Also, many techniques have been developed for the modification of nucleic acids with functional groups, including: fluorophores, chromophores, affinity labels, metal chelates, chemically reactive groups and enzymes. Smith et al., *Nature*, 321:674–679 (1986); Agarawal et al., *Nucleic Acids Research*, 14:6227–6245 (1986); Chu et al., *Nucleic Acids Research*, 16:3671–3691 (1988).

An impetus for developing both the synthesis and modification of nucleic acids has been the potential for their use in clinical diagnostic assays, an area also referred to as DNA probe diagnostics. Simple photonic mechanisms have been incorporated into modified oligonucleotides in an effort to impart sensitive fluorescent detection properties into the DNA probe diagnostic assay systems. This approach involved fluorophore and chemiluminescent-labeled oligonucleotides which carry out Förster nonradiative energy transfer. Heller et al., in "Rapid Detection and Identification of Infectious Agents," Kingsbury et al., eds., Academic Press, New York, N.Y. pp. 345–356 (1985). Förster nonradiative energy transfer is a process by which a fluorescent donor (D) group excited at one wavelength transfers its absorbed energy by a resonant dipole coupling process to a suitable fluorescent acceptor (A) group. The efficiency of energy transfer between a suitable donor and acceptor group has a $1/r^6$ distance dependency (see Lakowicz et al., in "Principles of Fluorescent Spectroscopy," Plenum Press, New York, N.Y., Chap. 10, pp. 305–337 (1983)).

In the work of Heller et al., supra, two fluorophore labeled oligonucleotides are designed to bind or hybridize to adjacent positions of a complementary target nucleic acid strand and then produce efficient fluorescent energy transfer in terms of re-emission by the acceptor. The first oligonucleotide is labeled in the 3' terminal position with a suitable donor group, and the second is labeled in the 5' terminal position with a suitable acceptor group. The binding or hybridization to the complementary sequence positions the fluorescent donor group and fluorescent acceptor groups so they are at optimal distance (theoretically) for most efficient Förster nonradiative energy transfer. However, the observed energy transfer efficiency in terms of re-emission by the acceptor was relatively low (~20%) for this particular arrangement.

In later work (Heller et al., European Patent Application No. EPO 0229943, 1987; and Heller et al., U.S. Pat. No. 4,996,143, Feb. 26, 1991), the advances in synthetic chemistry provided methods for the attachment of fluorophores at any position within an oligonucleotide sequence using a linker arm modified nucleotide. Also, with this synthetic linkage technique it was possible to incorporate both a donor and an acceptor fluorophore within the same oligonucleotide. Using the particular linker arm, it was found that the most efficient energy transfer (in terms of re-emission by the acceptor) occurred when the donor and acceptor were spaced by 5 intervening nucleotide units, or approximately 1.7 nm apart. Heller et al., U.S. Pat. No. 4,996,143 also showed that as the nucleotide spacing decreases from 4 to 0 units (1.4 nm to 0 nm), the energy transfer efficiency also decreases; which is not in accordance with Förster theory. As the nucleotide spacing was increased from 6 to 12 units (2 nm to 4.1 nm), the energy transfer efficiency was also found to decrease; which is in accordance with Förster theory. At the time, it was not explained nor understood why the more closely spaced donor and acceptor arrangements had reduced energy transfer efficiency and were not in agreement with Förster theory. In particular, the teachings of Heller et al. did not address multiple donor resonance and extended energy transfer from donors beyond Förster distances of >5 nm.

Fluorescent energy transfer has been utilized in other areas which include immunodiagnostics and liquid chromatography analysis. Morrison et al., *Anal. Biochem.*, 174:101–120 (1988); and Garner et al., *Anal. Chem.*, 62:2193–2198 (1990). Also, some of the initial demonstrations of simple fluorescent donor/ acceptor energy transfer in nucleic acids were later corroborated by other workers. Cardullo et al., *Proc. Natl. Acad. Sci. USA*, 85:8790–8794 (1988); and Morrision et al., *Anal. Biochem.*, 183:231–244 (1989). In the Cardullo et al. work, an arrangement is studied where two short (12-mer) oligonucleotide sequences, each terminally labeled with rhodamine acceptors and hybridized to a complementary 29-mer sequence, are associated with several intercalating donors (acridine orange). The arrangements described by Cardullo show some added energy transfer due to the additional donors. However, this increase in energy transfer efficiency is entirely consistent with direct donor to acceptor transfer, as none of the donors were described as functioning beyond the Förster distance necessary for efficient transfer. To date, there has been no descriptions of an organized structure capable of extended energy transfer from multiple donors and to an acceptor beyond normal Förster distances.

SUMMARY OF THE INVENTION

This invention relates to the design and synthesis of modified synthetic nucleic acid polymers/oligomers into which functional electronic/photonic properties are directly incorporated. In particular, it concerns incorporating the property of an extended nonradiative energy transfer process into arrangements of synthetic nucleic acids.

It has now been discovered that multiple chromophore donor groups which are located beyond the normal Förster distance (>5 nm) can be arranged to absorb and transfer photonic energy to a terminal acceptor group, thereby acting as a light antenna or photonic conductor. This property involves the ability of an array of donor groups to absorb photonic energy at one wavelength ($hv_1$), and directionally transfer it, via a coupled resonance process, to an acceptor group, where it is then re-emitted as photonic energy at a longer wavelength ($hv_2$). The selection and relative positioning of special donor chromophore groups, which include nonfluorescent chromophores, with appropriate acceptor fluorophores, leads to an efficient extended energy transfer process with unique properties. Additionally, appropriate designs for oligonucleotides and polynucleotides have found which allow a primary donor group to be placed in close proximity with an acceptor group.

Since the relative positions of the functional molecular components (chromophores) can be programmed, via their placement upon nucleotide sequences, nucleic acid containing the chromophores can be designed to self-assemble and organize into larger and more complex defined structures. The programmability and functional electronic/photonic properties of the molecular components enable connections, amplification mechanisms, and antenna arrays to be made within the nucleic acid structures. The combination of properties ultimately leads to the creation of photonic devices, photovoltaic devices, biosensors, and homogeneous and heterogeneous DNA diagnostic assay.

The present invention therefore describes a polynucleotide having at least two (multiple) donor chromophores operatively linked to the polynucleotide by linker arms, such that the chromophores are positioned by the linkage along the length of the polynucleotide at a donor—donor transfer distance. Typically the donor chromophores are nonfluorescing chromophores.

The polynucleotide can further contain a fluorescing acceptor chromophore operatively linked to the polynucleotide by a linker arm, wherein the fluorescing acceptor chromophore is positioned by the linkage at a donor-acceptor transfer distance from the donor chromophores such that the multiple donors can collect excitation light and transfer it to the acceptor which then re-emits the collected light.

In another embodiment the donor chromophores and acceptor chromophores can be displayed upon more than one polynucleotide such that upon their hybridization, the acceptor fluorescing chromophore is brought into donor-acceptor transfer distance to at least one of the donor chromophores. Thus, combinations of polynucleotides are contemplated containing preselected sequences and the requisite donor and acceptor chromophores that can be adapted for a variety of uses as described herein.

For example, a diagnostic assay system is described that contains a polynucleotide capable of donor—donor transfer as described above. The system can utilize an acceptor chromophore that is present on a separate polynucleotide, or the acceptor chromophore can be present on the same polynucleotide as the donor chromophores.

The sequences of the polynucleotides can be selected for purposes of complementary hybridization to facilitate assembly of larger structures capable of donor—donor transfer and ultimate donor-acceptor transfer. Alternatively, the sequences of the polynucleotides can be selected to be complementary to target nucleic acid sequences such that the polynucleotides are used diagnostically to detect the target sequences in samples.

In another embodiment, the invention describes structures in the form of a nucleic acid duplex that are comprised of at least two polynucleotides hybridized together by conventional complementary nucleotide base hybridization. Multiple polynucleotides can be hybridized to form the duplex as is represented in FIGS. 3A and 3B. The polynucleotides contain operatively linked donor and acceptor chromophores to provide a larger structure upon which the disclosed donor—donor and donor-acceptor energy transfers can occur. The chromophores can be arranged along a single strand of the duplex structure, but are preferably positioned such that the energy transfer alternates between the strands of the duplex.

Also contemplated is a biosensor device comprising a photonic energy sensing means and a polynucleotide of this invention having at least two donor chromophores operatively linked to the polynucleotide by linker arms, wherein the chromophores are positioned by the linkage along the length of the polynucleotide at a donor—donor transfer distance. The biosensor has at least one fluorescing acceptor chromophore operatively linked to the polynucleotide by a linker arm such that the fluorescing acceptor chromophore is positioned by the linkage at a donor-acceptor transfer distance from at least one of the donor chromophores. Furthermore, the polynucleotide is detectably positioned adjacent to the sensing means such that the sensing means can detect photonic energy emitted from the acceptor chromophore upon excitation of the donor chromophores.

In another embodiment, the invention contemplates a method for detecting the presence of a preselected nucleic acid sequence in a nucleic acid-containing sample that involves the use of one or more polynucleotides of this invention as a probe, and relying upon the energy transfer systems described herein for producing a detectable fluorescent acceptor emission to indicate a hybridization event.

Other embodiments will be apparent based on the disclosures herein.

BRIEF DESCRIPTION OF THE DRAWINGS

In the drawings forming a portion of this disclosure:

FIG. 4A shows the homogeneous system before the target DNA is denatured. Note that the acceptor group is proximal to the quencher group, and therefor emission from the acceptor is quenched. FIG. 4B shows the homogeneous system after the target DNA is denatured whereupon the multiple donor and acceptor oligomers have hybridized to the target DNA at specific, programmed, complementary sites to produce a structure capable of extended energy transfer.

DETAILED DESCRIPTION OF THE INVENTION

A. Chromophore-Containing Polynucleotides

Figure 1A:
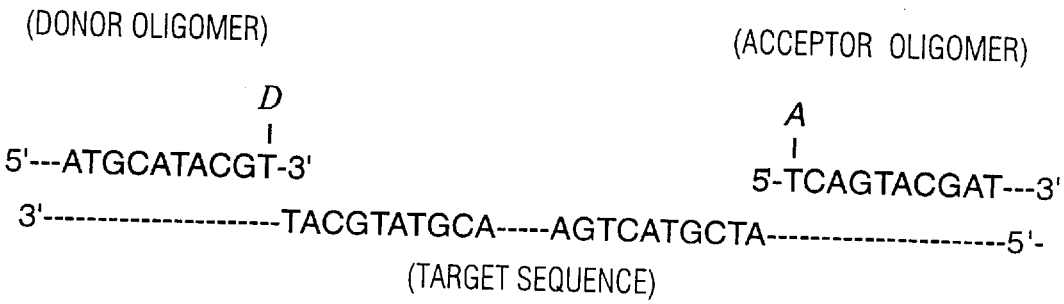
FIG. 1A illustrates how two chromophore-labeled oligonucleotides (donor oligomer SEQ ID NO 1 and acceptor oligomer SEQ ID NO 2) are designed to bind or hybridize to adjacent positions on a complementary target nucleic acid strand (target sequence SEQ ID NO 3). The exact nucleotide sequence and position of donor and acceptor groups is shown for the unhybridized (or disassociated system).

This invention relates to the design and synthesis of modified synthetic nucleic acid polymers/oligomers into which functional electronic/photonic properties are directly incorporated. Synthetic nucleic acids having inherent recognition properties (i.e., complementary hybridization) and are ideal materials for constructing molecular components which can self-organize into electronic and photonic structures and devices.

In one embodiment, the invention contemplates polynucleotide(s) having an acceptor chromophore group and one or more primary donor chromophores within F örster distance (<5 nm), and at least two donor chromophores, or preferably multiple chromophores located beyond normal Förster distance (>5 nm). Operatively acceptor and donor chromophores are linked to the polynucleotide(s) by linker arms, such that the chromophores are positioned along the length of the polynucleotide at donor—donor transfer distance (1.4 nm to 6.1 nm) effective for resonant energy transfer as described by the present discoveries.

The polynucleotides described herein can be formatted and used in a variety of configurations. The donor chromophores can be present on a single polynucleotide and the acceptor chromophore can be present on a separate polynucleotide that is only brought into donor-acceptor transfer distance by a preselected hybridization event. Alternatively, acceptor chromophores can be present on the same polynucleotide together with one or more of the donor chromophores.

In one embodiment, a polynucleotide has at least two donor chromophores operatively linked to the polynucleotide by linker arms such that the donor chromophores are positioned by the linkage along the length of the polynucleotide at a donor—donor transfer distance as defined herein. A preferred donor—donor transfer distance is about 1.4 nm to about 6.1 nm.

The polynucleotide(s) have a predetermined sequence selected to be complementary to other nucleic acid sequences, so that the chromophore containing polynucleotides can be programmed (1) to self-assemble with each other by the hybridization process, forming organized photonic or electronic structures on solid supports or thin films such as glass, silicon, germanium, gallium arsonide, polymers, resists, Langmuir Blodgett fluids and the like or (2) to bind to preselected target nucleic acid sequences in solution or attached to solid supports or thin film materials.

In one embodiment, a terminal or central polynucleotide further contains at least one fluorescing acceptor chromophore operatively linked to the polynucleotide by a linker arm, such that the fluorescing acceptor chromophore is positioned by linkage at a donor-acceptor transfer distance of from about 0.1 nm to about 1.7 nm from at least one primary or main coupling donor chromophore. These configurations provide the organized structures capable of extended nonradiative energy transfer described by the present invention.

For purposes of this invention and unless otherwise stated, the terms "oligonucleotide," "oligomer," or "polynucleotide" will refer generally to nucleic acids in the form of single-stranded nucleic acid polymers, comprised of DNA, RNA, or modified sequences produced by totally synthetic procedures. Technically, the shorter sequences from 2 to 50 nucleotides in length are referred to as oligonucleotides or oligomers, and the longer sequences (>50 nucleotides) are referred to as polynucleotides. However, for this invention the terms are used somewhat interchangeably insofar as they both denote nucleic acid polymers.

Important advantages of synthetic DNA as the support structure for providing the array to orient multiple donors and acceptor in a transfer structure are: (1) rapid synthesis with automated instruments, in lengths from 2 to 150 nucleotide units (0.7 nm to 50 nm); (2) programmable recognition with high specificity, via their nucleotide sequence; (3) easily modified with fluorophores, chromophores, affinity labels, metal chelates, and enzymes; (4) modifiable at any position in their sequence, and at several places within the base unit; (5) modifiable backbone structure to produce different properties (example; normally negatively charged DNA can be made in a neutral form); (6) linkable both covalently and noncovalently to solid surfaces: glass, metals, silicon, organic polymers, and bio-polymers; (7) reversible organizational properties; (8) ability to form three dimensional and branched structures; and (9) well understood and easily modeled structural and organizational properties.

1. Extended Energy Transfer

The particular functional electronic/photonic property which concerns this invention, is an extended nonradiative (Förster) energy transfer process. The basic Förster energy transfer process involves the ability of a donor group to absorb photonic energy at one wavelength ($hv_1$) and transfer it, via a nonradiative dipole coupling process, to an acceptor group which re-emits the photonic energy at a longer wavelength ($hv_2$). Energy transfer efficiency is dependent upon the parameters which are given in the equations below:

$$E = \frac{R_0^6}{R_0^6 + r^6} \quad (1)$$

$$R_o = 9.8 \times 10^3 (k^2 n^{-4} O_d J) \text{ (in Angstroms)} \quad (2)$$

where E=the transfer efficiency, r=the distance between the donor and acceptor, k is a dipole orientation factor, n is the refractive index of the medium, $O_d$ is the quantum yield of the donor, and J is the overlap integral which express the degree of overlap between the donor emission and the acceptor absorption. All other parameters being optimal, the $1/r^6$ dependency requires a donor to acceptor distance of less than 2 nm (20 Angstroms) for high efficient energy transfer to occur. Table 1 shows the theoretical energy transfer efficiencies by conventional Förster energy transfer (ET) when the donor (D) to acceptor (A) distance range is from 0 nm to 4.5 nm.

TABLE 1

| D/A Distance (nm) | Theoretical ET Efficiency (%) |
| --- | --- |
| 0 | 100 |
| 0.5 | 100 |
| 1.0 | 99 |
| 1.5 | 98 |
| 2.0 | 97 |
| 2.5 | 86 |
| 3.0 | 67 |
| 3.5 | 50 |
| 4.0 | 28 |
| 4.5 | <10 |

Figure 1B:
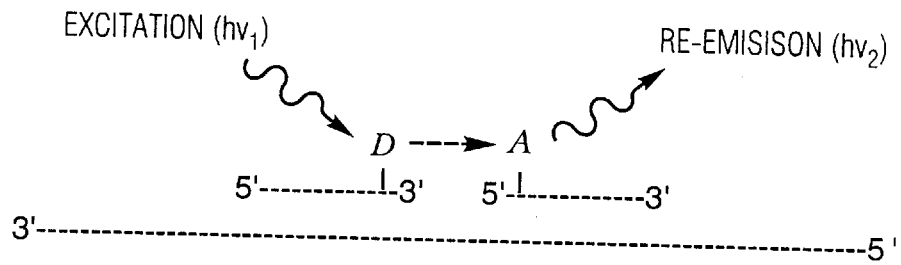
FIG. 1B illustrates the hybridized structure (or associated system). The binding or hybridization to the target sequence approximates the fluorescent donor group and fluorescent acceptor group at a preselected donor-acceptor transfer distance so that when the system is irradiated by photonic energy at $hv_1$ the donor group absorbs the energy and transfers it by nonradiative energy transfer (→) to the acceptor group which re-emits it at $hv_2$. Irradiating and emitting photons are indicated by the wavy-lined arrows.

FIG. 1 shows how two fluorophore-labeled oligonucleotides (a donor and an acceptor) are designed to bind or hybridize to adjacent positions of a complementary target nucleic acid strand and then produce efficient fluorescent energy transfer. Relative efficiencies for the energy transfer process can be expressed in two simplistic ways. The first is in terms of the ratio of transferred energy to the energy absorbed by the donor; this is determined by measuring the relative amount of donor fluorescence quenching that occurs in the presence of the acceptor. The second way expresses relative efficiency in terms of the ratio of energy re-emitted by the acceptor to the energy absorbed by the donor; this is determined by measuring the relative increase in acceptor fluorescence due to donor group. While both methods are considered relative measures of energy transfer efficiency, the efficient transfer of energy from the donor to the acceptor (seen as donor quenching), does not necessarily lead to the same efficiency for re-emission by the acceptor. This occurs when secondary processes (acceptor quenching) cause the acceptor to dissipate its energy other than by re-emission.

Extended energy transfer is the process by which multiple donor groups absorb photonic energy at one wavelength ($hv_1$) forming a coupled resonant structure which can directionally transfer the energy to an acceptor group. The resonant energy is then re-emitted as photonic energy at wavelength ($hv_2$). Under conditions where $hv_1$ is nonsaturating, photonic energy can be collected by arrays of donor groups and directionally transferred to an appropriate acceptor, greatly enhancing its fluorescent emission at $hv_2$. This can be considered a molecular antenna or amplifier mechanism. Alternatively, photonic energy ($hv_1$) can be collected at one end of a structure by a donor group and be transferred by a linear array of donors, to an acceptor group at the other end of the structure where it is re-emitted as $hv_2$. This type of molecular photonic transfer mechanism can be considered the equivalent of a photonic wire or connector. These mechanisms can also be used to interconnect different molecular structures, to connect molecular structures to surfaces, and to make molecular connections between surfaces (monolayers).

Thus, distances between donor chromophores are selected to provide a donor—donor transfer distance, which indicates that the transfer is a nonradiative energy transfer. Similarly distances between a terminal donor chromophore and the acceptor chromophore are selected to provide a donor-acceptor transfer distance, which indicates that the transfer by donor is nonradiative and results in the excitation of a fluorescing acceptor chromophore and subsequent emission spectrum from the acceptor.

2. Chromophores And Fluorophores

A novel part of this invention relates to the selection and positioning of special chromophore and fluorophore groups to form appropriate donor and acceptor pairs which are capable of energy transfer by dipole coupling.

A chromophore refers to those groups which have favorable absorption characteristics, i.e., are capable of excitation upon irradiation by any of a variety of photonic sources. Chromophores can be fluorescing or nonfluorescing. Nonfluorescing chromophores typically do not emit energy in the form of photonic energy ($hv_2$). Thus they can be characterized as having a low quantum yield, which is the ratio of emitted photonic energy to adsorbed photonic energy, typically less than 0.01. A fluorescing chromophore is referred to as a fluorophore, and typically emits photonic energy at medium to high quantum yields of 0.01 to 1.

Of particular importance to the present invention is the demonstration that nonfluorescent chromophores, such as 4-Dimethylaminophenyl-azophenyl-4'-isothiocyanate (or DABITC), can function as effective energy transfer donor groups. When these chromophore donor groups are closely approximated (0.1 nm to 1.7 nm) to a suitable acceptor group they produce a significant fluorescent re-emission by the acceptor. Chromophores capable of energy transfer to a suitable acceptor chromophore are referred to herein as donor chromophores or donors.

An acceptor chromophore for the purposes of the present invention is a fluorophore, that is capable of accepting energy transfer from a donor chromophore and producing an emission spectrum. Because energy transfer by dipole coupling can typically occur when there is an overlap in the emission spectrum of the donor and the excitation spectrum of the acceptor, a "suitable" acceptor typically has an excitation spectrum in the longer wavelengths than its corresponding suitable donor. In this regard, donors and acceptors can be paired for capacity to transfer energy on the basis of overlapping donor emission and acceptor excitation spectra. Therefore, potentially any chromophore can be paired with another chromophore to form an acceptor-donor pair, so long as the two chromophores have different emission spectrums, and have sufficiently overlapping donor emission and acceptor excitation spectra to effect energy transfer.

A nonfluorescent donor producing fluorescent re-emission in the acceptor group is an extremely valuable property. The nonfluorescing donor in a composition of the present invention provides the particular advantage of a low or absent level of emission by the donor, thereby not contributing to background or the detectable emitted light in a donor-acceptor system. Thus, nonfluorescent donors allow for very low background and are particularly preferred.

A multiple donor system comprised of such nonfluorescent chromophores would have very little inherent fluorescent background. This property overcomes a major limitation that has severely limited practical uses of fluorescent energy transfer in DNA diagnostic assay applications. It also opens opportunity to create more useful photonic mechanisms and applications.

With regard to unique properties in acceptors, most preferred are acceptors with the highest quantum yields, or with other properties that increase the signal-to-noise ratio between specific acceptor emissions and the background (nonspecific) emissions attributable to the donor. Examples of approaches to reduce the signal-to-noise ratio include using donors having lower emission, preferably nonfluorescing donors, selection of acceptor-donor pairs in which the spectral distance between the emission spectrum of the donor and acceptor is maximized, and preferably selected as to be non-overlapping, and the like approaches described further herein.

Table 2 lists some of the potential chromophores and fluorophores which can be used as donors, acceptors, and quenchers for the novel extended energy transfer mechanisms and applications disclosed in this invention. The list is not meant to be exclusive in that it identifies some specific types or classes of donors, acceptors, and quenchers which can produce these unique and desirable properties.

TABLE 2

CHROMOPHORE DERIVATIVES USEFUL AS DONORS, ACCEPTORS, OR QUENCHERS FOR THE EXTENDED ENERGY TRANSFER PROCESS AND RELATED PHOTONIC MECHANISMS

| DERIVATIVE[1] | (EX)[2] | (EM)[3] | (QY)[4] |
|---|---|---|---|
| 4,4'-Diisothiocyanatodihydro-stilbene-2,2'-disulfonic acid | 286 | none[5] | <0.01 |
| 4-acetamido-4'-isothiocyanato-stilbene-2,2'-disulfonic acid | 336 | 438 | M |
| 4,4'-Diisothiocyanatostilbene-2,2'-disulfonic acid | 342 | 419 | M |
| Succinimidyl pyrene butyrate | 340 | 375, 395 | 0.6 |
| Acridine isothiocyanate | 393 | 419 | M |
| 4-Dimethylaminophenylazophenyl-4'-isothiocyanate (DABITC) | 430 | none[5] | <0.01 |
| Lucifer Yellow vinyl sulfone | 438 | 540 | 0.2 |
| Fluorescein isothiocyanate | 494 | 520 | 0.5 |
| Reactive Red 4 (Cibacron Brilliant Red 3B-A) | 535 | none[5] | <0.01 |
| Rhodamine X isothiocyanate | 578 | 604 | M-H |
| Texas Red (Sulforhodamine 101, sulfonyl chloride) | 596 | 615 | H |

TABLE 2-continued

CHROMOPHORE DERIVATIVES USEFUL AS DONORS,
ACCEPTORS, OR QUENCHERS FOR THE EXTENDED ENERGY
TRANSFER PROCESS AND RELATED PHOTONIC MECHANISMS

| DERIVATIVE[1] | (EX)[2] | (EM)[3] | (QY)[4] |
|---|---|---|---|
| Malachite Green isothiocyanate | 629 | none[5] | <0.01 |
| IR144[6] | 745 | 825 | M |

[1]The fluorophores and chromophores listed above are shown in derivatized forms suitable for direct coupling to the primary amino group incorporated into the DNA polymer. In many cases other types of derivatives (succinimidyl esters and haloacetyl) are available for coupling to amines. Also, derivatives specific for coupling to sulfhydryl and aldehyde functional groups are available.
[2]EX is the absorption maximum in nanometers.
[3]EM is the emission maximum in nanometers.
[4]For quantum yields (QY) the approximate ranges are: "Low," 0.0–0.1; "Medium," 0.1–0.3; and "High," 0.3–1.0.
[5]These are essentially nonfluorescent (QY < 0.01) organic compounds, with medium to high molar absorptivity. They are more appropriately called chromophores.
[6]IR144 (Kodak Laser Dye) is underivatized, and requires modification before it can be coupled to a DNA polymer.

Particularly preferred donor chromophores are selected from the group consisting of 4,4'-Diisothiocyanatodihydrostilbene-2,2'-disulfonic acid, 4-acetamido-4'-isothiocyanatostilbene-2,2'-disulfonic acid, 4,4'Diisothiocyanatostilbene-2,2'-disulfonic acid, Succinimidyl pyrene butyrate, Acridine isothiocyanate, 4-Dimethylaminophenylazophenyl-4'-isothiocyanate (DABITC), Lucifer Yellow vinyl sulfone, Fluorescein isothiocyanate, Reactive Red 4 (Cibacron Brilliant Red 3B-A), Rhodamine X isothiocyanate, Texas Red (Sulforhodamine 101, sulfonyl chloride), Malachite Green isothiocyanate and IR1446. Exemplary donor chromophores are described in the Examples.

Particularly preferred fluorescing acceptor chromophores are selected from the group consisting of pyrene, Lucifer Yellow, acridine, riboflavin, fluorescein, rhodamine, Sulforhodamine 101, Texas Red and IR 144. Exemplary fluorescing acceptor chromophores are described in the Examples.

Also contemplated as useful donor or acceptor chromophores for the invention include those chromophores, derivatives of or combinations of, which would allow electronic signals such as excited electrons to enter the donor—donor transfer system and then be transferred as resonant energy to the acceptor and to exit the system as an electronic signal. In other words, the mechanism for input, exit, or both, into and out of the donor—donor-acceptor transfer system of this invention can involve chromophore(s) adapted to convert electronic energy into the resonant energy of the transfer system (and back again) such that the transfer system communicates to an electronic circuit. In this manner, an extended energy transfer system of the present invention can function as an electronic connector or signal conduit. Possible convertors between electronic energy and resonant energy include but are not limited to luminescent compounds, such as ruthenium complexes, photovoltaic cells, and the like.

3. Donor and Acceptor Pair Configurations

From the chromophores and fluorophores listed in Table 2 a number of donor/acceptor configurations or arrangements can be made that will produce efficient extended energy transfer processes and novel photonic mechanisms. These arrangements which are shown in Table 2 include:

(1) Arrangements of multiple donors groups (fluorescent and nonfluorescent) transferring energy to a single or smaller number of acceptor groups. Generally, multiple donors transfer to a single acceptor group, but under some conditions and for certain photonic mechanisms more than one acceptor group may be used. The preferred arrangements are those involving the nonfluorescent donors, which provide the important advantage of a low background extended energy transfer process. Other preferred arrangements involves multiple fluorescent donors, excited in the visible region, which transfer to an acceptor(s) which re-emits in the infrared region. This is a useful mechanism because the infrared emission can be detected by optoelectronic devices which are much less sensitive to background fluorescence produced in the visible region.

(2) Arrangements in which multiple donor groups (fluorescent and nonfluorescent) absorb light at $hv_1$, and transfer to an intermediate donor-acceptor, which then transfers to a final acceptor group, which re-emits at $hv_2$. These arrangements have the advantage of producing a large Stokes shift between the excitation wavelength ($hv_1$) and the emission wavelength ($hv_2$) of the system. This is important because the larger the separation between excitation and emission, the lower the background fluorescence for the system. Exemplary configurations are shown in Table 3, where three chromophores are shown in series. The preferred arrangements are those which transfer from nonfluorescent or fluorescent donors to an acceptor(s) which re-emit in the infrared region.

A preferred embodiment contemplates the use of IR144 (a Kodak Laser Dye), a chromophore that accepts excitation energy from donors that are excited in the visible region and then re-emits in the infrared region.

(3) Special arrangements in which certain chromophore groups with strong quenching properties are used to prevent fluorescent emission by the acceptor group. In this embodiment, the present invention contemplates the use of a quencher chromophore (or quencher), that has the capacity to accept, like an acceptor, the transfer of energy by dipole coupling, but does not have significant emission. Although similar in properties to a nonfluorescing donor, the term quencher refers to a nonfluorescing chromophore that is configured to draw the energy potential away from an excited acceptor so that the acceptor does not emit, i.e., the acceptor is quenched. An exemplary configuration utilizing a quencher chromophore in combination with a multiple donor oligonucleotide of the present invention is described in Example 3 and FIG. 4.

The mechanism for energy transfer to a quenching chromophore is the same as for donor—donor or donor-acceptor transfer, namely dipole coupling, and therefor is subject to the same requirements as described herein relating to transfer distances and optimum pairing configurations. Exemplary nonfluorescent chromophores suited for quenching are Reactive Red 4 or Malachite Green because they have no detectable emission and they are located at the "red" end of the spectrum, and therefore can be selected relative to a variety of acceptor chromophore to accept (quench) energy from the acceptor before it emits. The preferred arrangements are for the nonfluorescent chromophores Reactive Red 4 or Malachite to quench fluorescence in the Texas Red acceptor group.

TABLE 3

MULTIPLE DONOR/ACCEPTOR, MULTIPLE DONOR 1/ACCEPTOR
DONOR 2/ACCEPTOR, AND SPECIAL QUENCHING
ARRANGEMENTS

| DABITC | →[1] | Fluorescein |
|---|---|---|
| * DABITC | → | Texas Red |

TABLE 3-continued

MULTIPLE DONOR/ACCEPTOR, MULTIPLE DONOR 1/ACCEPTOR
DONOR 2/ACCEPTOR, AND SPECIAL QUENCHING
ARRANGEMENTS

| | | | | | |
|---|---|---|---|---|---|
| * DABITC | → | Texas Red | → | IR 144 | |
| Lucifer Yellow | → | Texas Red | | | |
| Lucifer Yellow | → | Fluorescein | → | Texas Red | |
| * Lucifer Yellow | → | Texas Red | → | IR 144 | |
| Fluorescein | → | Texas Red | | | |
| Fluorescein | → | IR 144 | | | |
| * Fluorescein | → | Texas Red | → | IR 144 | |
| * Texas Red | → | IR 144 | | | |
| * Malachite Green | →² | Texas Red | | | |
| * Reactive Red 4 | ⇄ | Texas Red | | | |

Figure 2A:
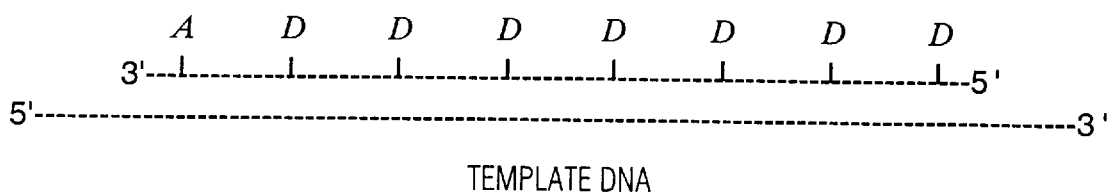
FIG. 2A illustrates a schematic representation of multiple donors groups (D) and a single acceptor group (A) incorporated into a single DNA polynucleotide strand hybridized or associated to a template DNA oligomer.

[1]The → indicates an energy transfer effect which leads to significant re-emission by the acceptor group.
[2]The ⇄ indicates an energy transfer effect that significantly quenches the fluorescence of the acceptor group.
* Preferred It is important to point out that the various arrangements and configurations of donor, acceptor, and quencher groups described above can be achieved by either incorporating them within a single DNA polymer; or by using a DNA template to assemble various combinations of multiple donor DNA polymers, acceptor DNA polymers, and quencher DNA polymers. Both types of arrangements are shown schematically in FIG. 2.

With regard to the optimum positioning or spacing of the primary "donor to acceptor" pair, thereby forming the donor-acceptor transfer distance, the basic $1/r^6$ distance dependency for Förster transfer requires a spacing of 0 to 5 nm, and preferably a spacing of about 0.1 nm to about 1.7 nm between the groups for efficient (~80–100%) energy transfer to occur. In terms of nucleotide spacing in single and double-stranded DNA polymers, this optimum transfer distance is roughly equivalent to 0 to 5 nucleotide units. At the shorter separation distances efficiency can theoretically approach 100%. At a distance >4.0 nm or 12 nucleotide units, energy transfer efficiency is less than 20%. For the primary donor to acceptor coupling, a close spacing (0, 1 or 2 base pairs) can be carried out, but requires special linker arm chemistries which orient groups for optimal energy transfer and eliminate any secondary quenching mechanisms or excitation traps.

With regard to the optimum positioning or spacing of the "donor to donor" pairs in multiple donor arrangements, thereby forming the donor—donor transfer distance, the incorporation of multiple donors at too close a spacing can interfere with the ability of the DNA to hybridize with high specificity. Also, close spacing of donor—donor pairs can sometime introduce secondary quenching mechanisms or excitation traps which can greatly reduce energy transfer efficiency. Presently, the best available chemistries for modifying a polynucleotide sequence at internal and terminal positions allows donor—donor spacings of about 4 to about 18 nucleotide units (1.4 nm to 6.1 nm) to be achieved over reasonably long distance. This would mean about 10 donors could be incorporated in a single oligonucleotide sequence of 50 nucleotides. Spacing at the longer intervals from 8 to 18 nucleotide units can be used, when hybridization of a complementary multiple donor polynucleotide produces a double-stranded structure with alternating donors now spaced at 4 to 9 nucleotide units. These alternating donor types of structures maintain reasonable transfer efficiency, reduce secondary donor—donor quenching, and interfere less with hybridization and stability of the organized structures.

In those case where quenching is a desired property, there can be 0 to 5 nucleotide unit (0.1 nm to 1.7 nm) spacing between the quencher group(s) and the acceptor group. It should be kept in mind that quencher-acceptor, donor-acceptor, as well as donor—donor pairs can also be formed between groups which are located on alternate sides of double-stranded DNA structures.

4. Synthesis and Labeling of Oligonucleotides and Polynucleotides

Synthesis of oligonucleotide and polynucleotide sequences can be carried out using any of the variety of methods including de novo chemical synthesis of polynucleotides such as by presently available automated DNA synthesizers and standard phosphoramidite chemistry, or by derivation of nucleic acid fragments from native nucleic acid sequences existing as genes, or parts of genes, in a genome, plasmid, or other vector, such as by restriction endonuclease digest of larger double-stranded nucleic acids and strand separation or by enzymatic synthesis using a nucleic acid template.

De novo chemical synthesis of a polynucleotide can be conducted using any suitable method, such as, for example, the phosphotriester or phosphodiester methods. See Narang et al., *Meth. Enzymol.*, 68:90 (1979); U.S. Pat. No. 4,356, 270; Itakura et al., *Ann. Rev. Biochem.*, 53:323–56 (1989); and Brown et al., *Meth. Enzymol.*, 68:109 (1979).

Derivation of a polynucleotide from nucleic acids involves the cloning of a nucleic acid into an appropriate host by means of a cloning vector, replication of the vector and therefore multiplication of the amount of the cloned nucleic acid, and then the isolation of subfragments of the cloned nucleic acids. For a description of subcloning nucleic acid fragments, see Maniatis et al., *Molecular Cloning: A Laboratory Manual*, Cold Spring Harbor Laboratory, pp. 390–401 (1982); and see U.S. Pat. Nos. 4,416,988 and 4,403,036.

In preferred embodiments, automated syntheses using an Applied Biosystems Model #381 DNA synthesizer and commercially available (Applied Biosystems) 5'-dimethoxytrityl nucleoside b-cyanoethyl phosphoramidite reagents and controlled pore glass synthesis columns were conducted for the work described in this patent application. In addition to the "standard phosphoramidite chemistry" other chemistries including RNA, hydrogen phosphonate, and phosphothioate may also be used.

Modified oligonucleotides with internal or terminal functional groups for subsequent labeling can be obtained in a number of ways. Several particularly useful methods to incorporate functional groups are described below. [For this particular section on synthetic procedures "incorporation of functional groups" means chemically reactive groups (primary amines, sulfhydryl groups, aldehydes, etc.) for subsequent coupling with fluorophores or chromophores. This should not be confused with "incorporation of functional properties" which in the main body of this invention concerns electronic/photonic properties.]

Internal functional primary amine groups can be incorporated at selected positions within the sequence and at the 3' and 5' terminal positions as suitably protected linker arm nucleosides (5'-dimethoxytrityl-5[N-(7-trifluoroacetylaminoheptyl)-2'-deoxyuridine 3'-O-phosphoramidite). This linker arm nucleoside (supplied by Glen Research) can be easily incorporated during the automated synthesis procedure. It provides a primary amine group for subsequent coupling reactions with various activated fluorophores and chromophores (the actual linker arm length is 1.5 nm).

Primary amine functionality can also be incorporated at the 5'-terminal position by using Aminolink 2. Aminolink 2 is a phosphoramidite molecule with a six carbon chain arm (0.9 nm) and a protected amine group (supplied by Applied Biosystems). This suitably protected linker group can be incorporated in the 5'-terminal position at the end of the automated synthetic procedure, providing a primary amine group for subsequent coupling reactions with various activated fluorophores and chromophores.

A different type of functionality can be incorporated at the terminal position by starting the synthetic procedure using a ribonucleoside, instead of a deoxyribonucleoside. This provides a ribonucleotide at the 3' terminal position of the oligomer, which subsequently can be oxidized with sodium periodate to form reactive aldehydes groups which can be coupled with a variety of fluorophores and chromophores.

These procedures for functionalizing oligonucleotides are not meant to be exclusive, as other procedures are available or can be developed to further enable the novel concepts of this invention.

At the end of each synthesis the finished oligonucleotide (modified or unmodified) is released from the support and blocking groups removed by treatment with concentrated ammonium hydroxide for 12 hours at 55° C. The dimethoxytrityl group can be left on the oligonucleotide to aid in the purification. The 5'-trityl oligonucleotide can be purified by reverse phase high pressure liquid chromatography (HPLC). The purity of each oligonucleotide product can be determined by analytical polyacrylamide gel electrophoresis. At this point the unmodified oligonucleotides are ready for experimental use. The oligonucleotides with reactive linker arm(s) can be reacted with the appropriate activated fluorophore.

Those fluorophore and chromophore derivatives containing isothiocyanate, sulfonyl chloride, succinimidyl ester, or triazine, can be easily coupled to oligonucleotides containing primary amine functional groups. Oligonucleotides containing 3'-terminal aldehydes (from periodate oxidized ribonucleotide) can be reacted with fluorophores and chromophores with primary amino or hydrazide groups. A wide variety of reagents and procedures exist for incorporating different fluorophores and chromophores into functionalized oligonucleotides [see: Bioconjugate Chemistry, Vol 1, #3, pp. 165–187 (1990); Symons, R. H., *Nucleic Acid Probes*, CRC Press, Inc. (1989); and Keller et al., *DNA Probes*, Stockton Press (1989)]. Also, direct fluorescent labeling of oligonucleotides (internal and terminal) can be carried out using fluorescent (fluorescein and acridine) phosphoramidites (Clontech). With this procedure a complete nucleotide is replaced by the fluorescent phosphoramidite derivative. These derivatives are incorporated during the normal automated DNA synthesis procedure.

5. Mechanisms, Devices, and Systems

It is important to emphasize that the programmability of the functional molecular components, via their nucleotide sequence, allows them to self-assemble and organize into larger and more complex defined structures. This programmability and the functional electronic/photonic properties of these molecular components enable photonic connections, amplification mechanisms, and antenna arrays to organize within the structures. The combination of properties ultimately leads to the creation of photonic devices, photovoltaic devices, biosensors, and homogeneous and heterogeneous DNA diagnostic assays.

Since a large number of DNA polymers each containing a number of donor groups can be organized together, it is possible to build relatively large antenna or amplifier networks, or to make long photonic transfers and connections. With regard to extended energy transfer for amplification or antenna functions; the number of donors to an acceptor in a given molecular structure or system depends on several factors. These include: (1) the light flux (intensity) impinging on the final system; (2) the overall energy transfer efficiency for the donor arrays, (3) the quantum yield (QY) of the donors and the acceptors, and (4) the life time ($\tau$) of the donor and acceptor excited states. For antenna or photonic amplification applications, at low to intermediate light levels, the number of donors to acceptor could range from the lower limit of 2 to 1, and preferably 10 to 1, to the upper limit of $10^6$ to 1. For heterogeneous DNA diagnostic and Biosensor applications, the number of donors to an acceptor could range from the lower limit of 2 to 1, and preferably 5 to 1, to the upper limit of $10^5$ to 1. For homogenous DNA diagnostic applications using the typical mercury or xenon light sources found in the standard spectrofluorometers or other instruments for fluorescent analysis, the number of donors to an acceptor could range from the lower limit of 2 to 1 to the upper limit of $10^4$ to 1. Also, for some photonic mechanisms and certain device applications, a multiple donor DNA polymer(s) may transfer to an acceptor DNA polymer which has more than one acceptor group. The same basic ratios of donors to acceptor that were given above apply to the those molecular structures or systems which have an acceptor DNA polymer with more than one acceptor group.

Figure 3A:
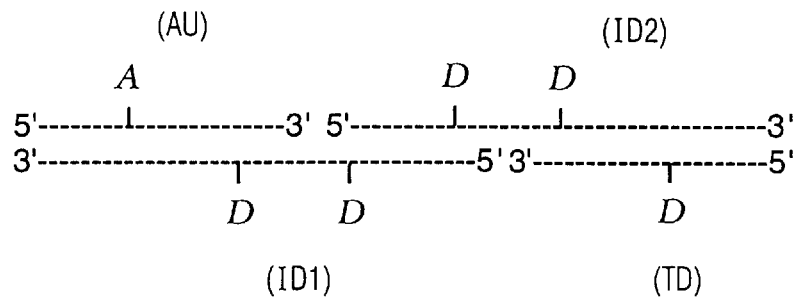
FIG. 3A illustrates schematically the exemplary 14 nm photonic antenna structure described in Example 1 that is assembled and organized from four oligonucleotides: the 16-mer acceptor unit (AU), the 30-mer intermediate donor 1 unit (ID1), the 29-mer intermediate donor 2 unit (ID2), and the terminal donor unit (TD).
Figure 3B:
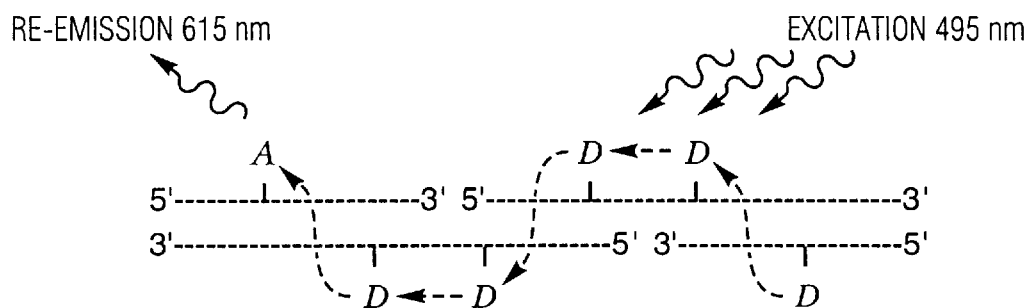
FIG. 3B illustrates extended energy transfer when the assembled structure is illuminated wit light at 495 nm. The wavy lines indicate irradiating or emitting photons and the dashed arrow (→) shows the direction of the extended energy transfer process.

A device of this invention can be described in terms of a duplex nucleic acid structure, that is two or more polynucleotides hybridized by conventional complementarity to form the typical double stranded duplex, except that a "strand" of the duplex can be comprised of two or more adjacent polynucleotides as shown in FIG. 3.

A duplex nucleic acid structure of this invention is therefore comprised of at least two hybridized polynucleotides. The structure has (1) at least two donor chromophores operatively linked to the structure by linker arms attached to a polynucleotide of the structure such that the donor chromophores are positioned by the linkage along the length of the structure at a donor—donor transfer distance. The structure also has (2) at least one fluorescing chromophore operatively linked to the structure by a linker arm attached to a polynucleotide of the structure such that the fluorescing chromophore is positioned by the linkage at a donor-acceptor transfer distance from at least one of the donor chromophores.

As suggested by the configuration shown in FIG. 3, one embodiment can involves the use of one or more alternating chromophores. That is, the structure contains donor chromophores that are alternately positioned on the structure such that said donor—donor transfer distance can cross (alternates) between polynucleotides of the duplex. The alternating configuration can be such that some donor—donor transfers are between adjacent donors on the same polynucleotide and some are between donors on opposite duplex strands (i.e., alternating), or such that all the transfers are alternating. The alternating transfer distance can be expressed in terms of a donor—donor transfer distance, as described herein, or can be expressed in terms of nucleotide base spacing. Thus, for example, a structure with alternating donor chromophores is contemplated that comprises at least three donor chromophores wherein the donor chromophores are positioned from 4 to 18 nucleotide base units apart on a single polynucleotide.

Another embodiment is the use of the capability of extended photonic energy transfer across multiple donors as a photonic energy transfer system or circuit. The photonic energy transfer system can have one or more of the polynucleotide components described herein. Thus a photonic energy transfer system comprises a polynucleotide having at least two donor chromophores as described before. The polynucleotide may also contain an acceptor chromophore. The system may comprise one or more additional polynucleotides in the various configurations described herein.

Insofar as the present invention describes structures and systems for extended photonic energy transfer, it is to be understood that one embodiment contemplates the use of the described structures, polynucleotides, multi-polynucleotide duplexes, photonic energy transfer systems and the like, in a solid state. That is, a polynucleotide(s) of the system can be operatively linked (attached) to a solid support to facilitate the use of the extended energy transfer device. Solid support systems are particularly suited for electronic devices, such as photonic energy collectors, light amplifiers, energy transfer conduits, and the like.

Attachment of a polynucleotide to a solid support can by any of a variety of means and is not to be construed as limiting. Exemplary attachment means are described elsewhere herein, and are generally well known to one skilled in the polynucleotide arts.

In one embodiment, a solid support can represent a passive support, that is the support acts passively to only hold the energy transfer polynucleotide in the solid phase. In another embodiment, a solid support can be active, that is the support provides a complementary function such as to donate energy to the transfer system, or to have the capacity to detect, receive, convert, translate or transmit the emitted photonic energy from the acceptor to a second circuit. An exemplary second circuit is a photosensor, photovoltaic, and the like device in the solid phase medium.

B. Diagnostic Systems and Methods

1. Diagnostic Systems

A diagnostic system in kit form of the present invention includes, in an amount sufficient for at least one assay, a chromophore-containing polynucleotide of the present invention, as a separately packaged reagent. Instructions for use of the packaged reagent are also typically included.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In one embodiment, the invention contemplates a diagnostic system for photonic detection of a preselected nucleotide sequence comprising, in an amount sufficient for at least one assay, a polynucleotide having at least two donor chromophores operatively linked to the polynucleotide by linker arms, wherein the donor chromophores are positioned by linkage along the length of said polynucleotide at a donor—donor transfer distance. The polynucleotide is designed to hybridize to the preselected nucleotide sequence (i.e., the target nucleic acid sequence), and therefore contains a nucleotide sequence complementary to the target nucleic acid sequence. Target nucleic acid sequence complementarity is well known in the nucleic acid diagnostic arts as it applies to a reagent polynucleotide (i.e., probe), and therefore need not be described in detail.

In another embodiment, the polynucleotide of a diagnostic system further contains at least one fluorescing chromophore operatively linked to the polynucleotide by a linker arm, such that the fluorescing chromophore is positioned by linkage at a donor-acceptor transfer distance from at least one of the donor chromophores. In this embodiment, both the acceptor and multiple donor chromophores are present on a single polynucleotide. Exemplary is the structure shown in FIG. 2(a).

In another embodiment, a diagnostic system includes a second polynucleotide containing at least one fluorescing chromophore operatively linked to said second polynucleotide by a linker arm. Exemplary is the structure shown in FIG. 2(b).

In a further embodiment, a diagnostic system also contains, typically in a separate container, a quencher polynucleotide of the present invention. The included quencher polynucleotide is complementary to at least a portion of the acceptor polynucleotide, and preferably is completely complementary to the acceptor polynucleotide. A quencher polynucleotide must be shorter in length that an acceptor polynucleotide, typically at least 10 percent shorter, and more preferably at least 50 percent shorter, to assure that the acceptor will preferentially hybridize to a target sequence if present in the hybridization admixture.

The reagent species, i.e., chromophore-containing polynucleotide of the invention, of any diagnostic system described herein can be provided in solution, as a liquid dispersion or as a substantially dry power, e.g., in lyophilized form. A solid support as a reaction vessel and one or more buffers can also be included as separately packaged elements in this diagnostic assay system.

The packages discussed herein in relation to diagnostic systems are those customarily utilized in diagnostic systems. The term "package" refers to a solid matrix or material such as gloss, plastic, paper, foil and the like capable of holding within fixed limits a diagnostic reagent of the present invention. Thus, for example, a package can be a glass vial used to contain a contemplated diagnostic reagent.

2. Diagnostic Methods

The present invention also contemplates any diagnostic method that results in detecting emitted photonic energy produced by an chromophore-containing structure of the present invention. Insofar as the emission is a result of excitation and subsequent energy transfer from the excited donor chromophores to the acceptor chromophore, the present method comprises at least two steps:

(1) excitation of an organized structure of this invention that contains at least two donor chromophores operatively linked to a support structure by linker arms, such that the donor chromophores are positioned along the length of the support at a donor—donor transfer distance, and also contains at least one fluorescing acceptor chromophore operatively linked to the support structure by a linker arm at a position on the structure that provides a donor-acceptor transfer distance from at least one of the donor chromophores. The excitation is an amount of photonic energy sufficient to induce nonradiative energy transfer between the donor chromophores as a "collecting" event, and to induce nonradiative energy transfer between the donor chromophore and the acceptor chromophore such that the acceptor itself is excited sufficient to result in emission of photonic energy.

(2) detection of the resulting emitted photonic energy by the use of any of a variety of photonic sensors.

The organized structure containing the chromophores as described above can be any of the various configurations described herein. The particular excitation means and sensing means can vary widely depending on the needs of the system at hand, and depend upon sensitivity required, the excitation and emission characteristics of the incorporated donor and acceptor chromophores, and the application of the structure.

In a particularly preferred diagnostic method, the present invention contemplates a method of photonic detection of preselected nucleic acid sequences using chromophore-containing polynucleotides of the present invention as hybridization probes for detecting a target sequence in a sample containing nucleic acids.

Thus a diagnostic method for detecting the presence of a preselected nucleic acid sequence in a nucleic acid-containing sample is contemplated comprising the steps of:
(a) admixing:
   (i) a polynucleotide having (1) at least two donor chromophores operatively linked to a polynucleotide by linker arms, such that the chromophores are positioned by linkage along the length of the polynucleotide at a donor—donor transfer distance, and (2) at least one fluorescing acceptor chromophore operatively linked to the polynucleotide by a linker arm, such that the fluorescing acceptor chromophore is positioned by linkage at a donor-acceptor transfer distance from at least one of the donor chromophores, wherein the polynucleotide has a nucleotide sequence that is preselected as to be complementary to the preselected "target" nucleic acid sequence; with
   (ii) a nucleic acid-containing sample containing the preselected nucleic acid base ("target") sequence to form a hybridization reaction admixture;
(b) subjecting the hybridization reaction admixture to hybridization conditions for a time period sufficient for the polynucleotide to hybridize to the target sequence and form a donor chromophore containing- and acceptor chromophore containing-hybridized nucleic acid duplex;
(c) exciting the donor chromophore in the nucleic acid duplex formed in step (b) by exposing the donor chromophore to sufficient photonic energy to induce emission of photonic energy from the acceptor chromophore; and
(d) detecting the presence of photonic energy emitted from the excited acceptor chromophore, thereby detecting the presence of the preselected nucleic acid sequence in the sample.

In a related embodiment, the admixing of step (a) differs in that instead of a single polynucleotide containing both the multiple acceptors and at least one acceptor chromophores, the donors are present on one or more polynucleotides separate from the polynucleotide containing the acceptor chromophore.

Figure 2B:
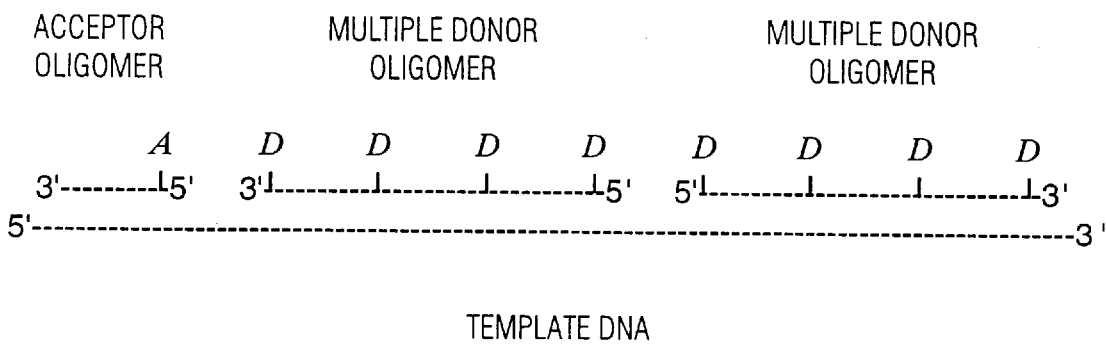
FIG. 2B illustrates a multiple donor DNA polymer and an acceptor DNA polymer assembled into an organized structure on a template DNA polymer.

In this embodiment, illustrated in FIG. 2(b) and in FIG. 3, the positioning of the donors and the acceptor are controlled both by their linkage position on their respective polynucleotides, and on the proximation of those chromophores upon hybridization to a preselected nucleic acid target sequence.

In another embodiment, the hybridization admixture can contain a quencher polypeptide as described herein, having a nucleic acid sequence designed to compete with the target sequence for hybridization with the polynucleotide containing the target nucleic acid sequence. The embodiment is shown in Example 3 and FIG. 4.

A hybridization reaction mixture is prepared by admixing effective amounts of a polynucleotide probe or probes of this invention, a target nucleic acid and other components compatible with a hybridization reaction admixture.

Target nucleic acid sequences to be hybridized in the present methods can be present in any nucleic acid-containing sample so long as the sample is in a form, with respect to purity and concentration, compatible with nucleic acid hybridization reaction. Isolation of nucleic acids to a degree suitable for hybridization is generally known and can be accomplished by a variety of means. For instance, nucleic acids can be isolated from a variety of nucleic acid-containing samples including body tissue, such as skin, muscle, hair, and the like, and body fluids such as blood, plasma, urine, amniotic fluids, cerebral spinal fluids, and the like. See, for example, Maniatis et al., *Molecular Cloning: A Laboratory Manual*, Cold Spring Harbor Laboratory (1982); and Ausubel et al., *Current Protocols in Molecules Biology*, John Wiley and Sons (1987).

The hybridization reaction mixture is maintained in the contemplated method under hybridizing conditions for a time period sufficient for the polynucleotide probe to hybridize to complementary nucleic acid sequences present in the sample to form a hybridization product, i.e., a complex containing the chromophore-containing polynucleotide probe(s) of this invention and target nucleic acid.

The phrase "hybridizing conditions" and its grammatical equivalents, when used with a maintenance time period, indicates subjecting the hybridization reaction admixture, in the context of the concentrations of reactants and accompanying reagents in the admixture, to time, temperature and pH conditions sufficient to allow the polynucleotide probe to anneal with the target sequence, typically to form a nucleic acid duplex. Such time, temperature and pH conditions required to accomplish hybridization depend, as is well known in the art, on the length of the polynucleotide probe to be hybridized, the degree of complementarity between the polynucleotide probe and the target, the guanidine and cytosine content of the polynucleotide, the stringency of hybridization desired, and the presence of salts or additional reagents in the hybridization reaction admixture as may affect the kinetics of hybridization. Methods for optimizing hybridization conditions for a given hybridization reaction admixture are well known in the art.

Typical hybridizing conditions include the use of solutions buffered to pH values between 4 and 9, and are carried out at temperatures from 18 degrees C. (18° C.) to 75° C., preferably about 37° C. to about 65° C., more preferably about 54° C., and for time periods from 0.5 seconds to 24 hours, preferably 2 minutes.

Hybridization can be carried out in a homogeneous or heterogeneous format as is well known. The homogeneous hybridization reaction occurs entirely in solution, in which both the polynucleotide probe and the nucleic acid sequences to be hybridized (target) are present in soluble forms in solution. A heterogeneous reaction involves the use of a matrix that is insoluble in the reaction medium to which either the polynucleotide probe or target nucleic acid is bound. For instance, the body sample to be assayed can be affixed to a solid matrix and subjected to in situ hybridization.

In situ hybridization is typically performed on a body sample in the form of a slice or section of tissue usually having a thickness in the range of about 1 micron to about 100 microns, preferably about 1 micron to about 25 microns and more preferably about 1 micron to about 10 microns. Such sample can be prepared using a commercially available cryostat.

Alternatively, a heterogeneous format widely used is the Southern blot procedure in which genomic DNA is electrophoresed after restriction enzyme digestion, and the electrophoresed DNA fragments are first denatured and then transferred to an insoluble matrix. In the blot procedure, a polynucleotide probe is then hybridized to the immobilized genomic nucleic acids containing complementary nucleic acid (target) sequences.

Still further, a heterogeneous format widely used is a library screening procedure in which a multitude of colonies, typically plasmid-containing bacteria or lambda bacteriophage-containing bacteria, is plated, cultured and blotted to form a library of cloned nucleic acids on an insoluble matrix. The blotted library is then hybridized with a polynucleotide probe to identify the bacterial colony containing the nucleic acid fragments of interest.

Typical heterogeneous hybridization reactions include the use of glass slides, nitro-cellulose sheets, and the like as the solid matrix to which target-containing nucleic acid fragments are affixed.

Also preferred are the homogeneous hybridization reactions such as are conducted for a reverse transcription of isolated MRNA to form cDNA, dideoxy sequencing and other procedures using primer extension reactions in which polynucleotide hybridization is a first step. Particularly preferred is the homogeneous hybridization reaction in which a specific nucleic acid sequence is amplified via a polymerase chain reaction (PCR).

Where the nucleic acid containing a target sequence is in a double-stranded (ds) form, it is preferred to first denature the dsDNA, as by heating or alkali treatment, prior to conducting the hybridization reaction. The denaturation of the dsDNA can be carried out prior to admixture with a polynucleotide to be hybridized, or can be carried out after the admixture of the dsDNA with the polynucleotide. Where the polynucleotide itself is provided as a double-stranded molecule, it too can be denatured prior to admixture in a hybridization reaction mixture, or can be denatured concurrently therewith the target-containing dsDNA.

The amounts of polynucleotide admixed to a hybridization reaction admixture can vary widely, and depends on the application, which in turn depends on the sensitivity required for detection of the target sequence. For homogeneous hybridization admixtures, the chromophore-containing polynucleotides can be present in concentrations of about 1 to 1000 nanograms (ng) per milliliter (ml), and preferably about 10 to 100 ug/ml where the polynucleotide is of about 20 nucleotides in length.

In terms of the amount of acceptor chromophore present on a subject polynucleotide, in homogeneous liquid hybridization admixtures the level of detection for a single acceptor chromophore per polynucleotide is at least about $10^4$ to $10^5$ acceptor chromophore molecules per 100 microliters ($\mu$l).

For heterogeneous hybridization admixtures, such as where the target nucleic acid is present in the solid phase, the chromophore-containing polynucleotides are added to the hybridization admixture in amounts of at least about $10^6$ to $10^7$ molecules of acceptor chromophore per band of nucleic acid to be detected, or per 2 millimeter (mm) dot blot of target nucleic acid. An exemplary application is to detect nucleic acid segments present on a Southern blot or a DNA sequencing gel using, for example, an ABI sequence reader that detects fluorometrically labelled probes.

C. Photonic Devices

The present invention provides for photonic devices such as light collectors and photonic conductors, by virtue of the capacity of the multiple donor transfer structure to be extended over long distances. Thus the structure can be designed as a linear conductor of photonic energy, or can be configured as an light-sensitive photonic switch, i.e., a biosensor.

Thus in one embodiment, the present invention contemplates a biosensor comprising a polynucleotide of the present invention having at least two donor chromophores operatively linked to said polynucleotide by linker arms, wherein said chromophores are positioned by said linkage along the length of said polynucleotide at a donor—donor transfer distance. the polynucleotide also has at least one fluorescing acceptor chromophore operatively linked to said polynucleotide by a linker arm, wherein said fluorescing acceptor chromophore is positioned by said linkage at a donor-acceptor transfer distance from at least one of said donor chromophores.

Thus the biosensor contains a photon collector that can be a variety of lengths, delivering the collected and transferred photonic energy to the acceptor chromophore. Preferably, a biosensor contains multiple acceptor chromophores clustered to provide a brighter photonic output.

Positioned adjacent to the acceptor or cluster of acceptors is a photon sensing means to detect the presence of emitted photonic energy. The sensing means can be any of a variety of light detecting devices, such as a photomultiplier tube, a fiber optic system that delivers the emitted light to a light sensitive photomultiplier, and the like sensing means.

EXAMPLES

The following examples are intended to illustrate, but not limit, the present invention.

1. Design and Synthesis of a Self-Organizing Extended Energy Transfer System

Five different specific sequence fluorescent oligonucleotides and non functionalized versions of the same sequences were designed and synthesized for the experimental demonstration of an extended energy transfer system. These include the following:

(1) An acceptor 16-mer oligonucleotide unit, 5.4 nm in length, labelled with Sulforhodamine 101 (AU).

(2) A first intermediate donor 30-mer oligonucleotide unit, 10.2 nm in length, labelled with two fluoresceins separated by a spacing of 6 nucleotides or 2.4 nm (ID1).

(3) A second intermediate donor 29-mer oligonucleotide unit, 9.9 nm in length, labelled with two fluoresceins separated by a spacing of 6 nucleotides or 2.4 nm (ID2).

(4) A repeater intermediate donor 30-mer oligonucleotide unit, 10.2 nm in length, labelled with two fluoresceins separated by a spacing of 7 nucleotides or 2.7 nm, (RD). The repeater unit is designed so that the structure can be extended.

(5) A terminal donor 15-mer oligonucleotide unit, 5.1 nm in length, labelled with a single fluorescein (TD).

The unmodified versions of all the above oligonucleotides were also synthesized. All of the oligonucleotides are designed by their encoded sequence to bind to complementary portions of each other, to form linear double stranded structures. The specific sequence and position of the fluorescent label(s) [A=Sulforhodamine 101 (Texas Red), D=Fluorescein] in the five modified oligonucleotide sequences are shown below and labelled as SEQ ID NOs 4–8, respectively:

1) AU    5'-ATGTCTGACTGCAGCT-3'

20 ID1    5'-ACGACCATAGTGCGAGCTGCAGTCAGACAT-3

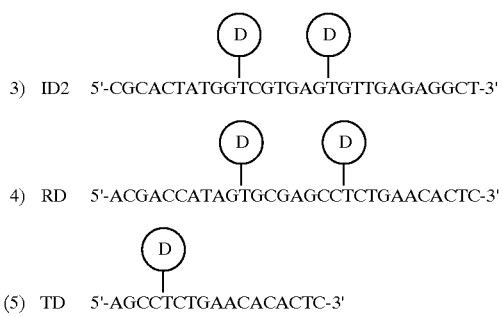

3) ID2  5'-CGCACTATGGTCGTGAGTGTTGAGAGGCT-3'

4) RD  5'-ACGACCATAGTGCGAGCCTCTGAACACTC-3'

(5) TD  5'-AGCCTCTGAACACACTC-3'

The oligonucleotide sequences shown above and the nonfunctionalized versions were all synthesized on an Applied Biosystems Automated DNA Synthesizer, Model #381, using standard phosphoramidite chemistry on controlled pore glass support. In the case of the functionalized oligonucleotides the protected linker arm nucleoside (5'-dimethoxytrityl-5-trifluoroaminoalkyl deoxyuridine) was incorporated at the selected position(s) indicated above. This linker arm nucleoside provides a primary amine group for reaction with the activated fluorophores, Sulforhodamine 101 sulfonyl chloride (Texas Red) and fluorescein isothiocyanate (FITC).

At the end of each synthesis the finished oligonucleotide was released from the support and blocking groups removed by treatment with concentrated ammonium hydroxide for 12 hours at 55° C. The dimethoxytrityl group was left on the oligonucleotide to aid in the purification. The 5'-trityl oligonucleotide was purified by reverse phase high pressure liquid chromatography (HPLC). The purity of each oligonucleotide product was determined by analytical polyacrylamide gel electrophoresis.

The HPLC-purified and unmodified oligonucleotides were ready for experimental use. The oligonucleotides containing the reactive linker arm(s) were then reacted with the appropriate activated fluorophore. Fluorescent labeling was carried out by reacting ~500 ng of the oligonucleotide containing the reactive linker arm with 1 mg of either Sulforhodamine 101 sulfonyl chloride (Texas Red) or Fluorescein isothiocyanate (both available from Molecular Probes) in 100 $\mu$l of 0.1M sodium bicarbonate (pH 8.5) for 2 hours at 20° C. After the reaction was complete the excess fluorophore reagent was removed by passing the solution through a Sephadex G-25 gel filtration column. The final purification of the fluorescent-labeled oligonucleotides from unlabeled material was carried out by preparative polyacrylamide gel electrophoresis.

The UV/Visible spectra (240 nm to 600 nm) were obtained (Hewlett Packard 8451A Diode Array Spectrophotometer) for all purified fluorescent and unmodified oligonucleotides. From the spectral data the concentrations, and the degree of fluorescent labeling were determined. The Acceptor Unit (AU) was determined to be >95% pure in terms of sulforhodamine 101 (Texas Red) labeling. The Intermediate Donor 1 (ID1) was determined to be about 40% pure in terms of the double fluorescein labeled component, the remainder was a mix of the single labeled components. The Intermediate Donor 2 (ID2) was determined to be about 30% pure in terms of the double fluorescein labeled component, the remainder was a mix of the single labeled components. The Repeat Donor (RD) unit was determined to be about 25% pure in terms of the double fluorescein labeled component, the remainder a mix of the single labeled components. The Terminal Donor (TD) was determined to be >95% pure in terms of fluorescein labeling. While the Intermediate Donors were not fully doubled labeled with fluorescein, they still are suitable for demonstrating the extended energy transfer mechanism in a self-organizing system.

The actual experiments designed to show extended energy transfer herein involve organizing a 14 nm long photonic antenna structure, via hybridization, of the four oligonucleotide units: the acceptor unit (AU), the intermediate donor 1 unit (ID1), the intermediate donor 2 unit (ID2), and one terminal donor unit (TD). The organized structure and the path for extended energy transfer are show in FIG. 3.

The assembled structure of the 14 nm antenna structure was formed by combining the above oligonucleotides at a concentration of 0.5 nanomole/$\mu$l in 500 $\mu$l of aqueous buffer (0.1M Sodium chloride/0.02M sodium phosphate, pH 7.8) at 20° C. These conditions are optimal for the oligonucleotide units to quickly hybridize (one minute) to their complementary sequences and self-organize (assemble) the 16 nm linear double stranded structures.

A number of experimental control structures were also assembled with the same basic arrangement, except one or more of the donor units utilized was in the unlabeled (NL) form. Fluorescein and Sulforhodamine 101 were picked as the fluorescent donor and acceptor groups because of the potential for reasonably efficient Förster energy transfer. The organized 14 nm antenna structure is designed to have a 6 base pair (2.4 nm) spacing (acceptor-donor transfer distance) between the Sulforhodamine group in the acceptor unit AU) and the first fluorescent group in the intermediate donor 1 unit (ID1), and to have a 6 base pair spacing (donor—donor transfer distance) between each of the fluorescein donors in the rest of the array.

Fluorescein has its absorption (excitation) maximum at 495 nm wavelength ($EX_{495}$), its emission maximum at 520 nm wavelength ($EM_{520}$), and an extinction coefficient of ~72,000. Sulforhodamine 101 (Texas Red) has its absorption (excitation) maximum at 595 nm wavelength ($EX_{595}$), its emission maximum at 615 nm wavelength ($EM_{615}$), and an extinction coefficient of ~85,000. Fluorescein's broad emission band spans from 500 nm out to 600 nm, and has good overlap with sulforhodamine's broad absorption band which spans from 520 nm to 600 nm. This overlap of the emission and adsorption bands and high quantum yield of each of the fluorophores make them a good pair for energy transfer.

The demonstration of extended energy transfer in the assembled photonic antenna structure was carried out by exciting the fluorescein donor units with radiation at 495 nm, and measuring the re-emission of radiation at 615 nm by the sulforhodamine 101 acceptor unit. The base Texas Red fluorescent emission at 615 nm was determined by exciting at 595 nm (an Aminco-Bowmen Spectro-fluorometer was used to carry out these experiment). The relative energy transfer efficiency (ET eff.) is the ratio of the 615 nm emission when the system is excited at 495 nm to the 615 nm emission when excited at 495 nm multiplied by 100, and can be represented by the formula:

$$ET \text{ eff.} = EM_{615}(EX_{495})/EM_{615}(EX_{595}) \times 100 \quad (3)$$

Demonstration of reversibility of self-organization of the 16 nm photonic antenna structure was carried out by first assembling the organized structure at 20° C., then heating it to 90° C. for one minute, and then cooling the system back to 20° C. (one minute). Excitation and emission measurements were conducted as before for each condition after the processes of assembly (initial), heating (heated) and cooling (cooled). The results for the experimental demonstrations of extended energy transfer in the various arrangements, and for the reversible self-assembly are given in Table 4.

TABLE 4

RESULTS OF EXTENDED ENERGY TRANSFER EXPERIMENTS

| STRUCTURE[1] | TEMP (°C.) | EX (nm) | E.T. Eff. (%) |
|---|---|---|---|
| AU/ID1/ID2/TD | 20 | 495 | 76 |
| AU/ID1/ID2 (ND/TD (NL) | 20 | 495 | 46 |
| AU/ID1 (NL)/ID2/TD | 20 | 495 | 8 |
| AU/ID1 (NL)/ID2 (NL)/TD (NL) | 20 | 495 | 4 |
| AU/ID1 (NL)/ID2 (NL)/TD (NL) | 20 | 595 | 100 |
| AU/ID1/ID2/TD[2] (initial) | 20 | 495 | 73 |
| AU/ID1/ID2/TD[2] (heated) | 90 | 495 | 6 |
| AU/ID1/ID2/TD[2] (cooled) | 20 | 495 | 77 |

[1]AU = acceptor unit with Sulforhodamine 101; ID1 = the intermediate donor 1 with two fluoresceins; ID2 = the intermediate donor 2 with two fluoresceins; TD = the terminal donor with one fluorescein; NL means the oligomer was not labeled (no fluorescein donor groups).
[2]Experiments demonstrating reversible self-assembly, initially at 20° C., heat to 90° C., and cooled back to 20° C.

Extended energy transfer is shown in Table 4 to be occurring in the organized (AU/ID1/ID2/TD) antenna structure producing about a 76% energy transfer efficiency to the acceptor unit (AU) when all the donor units present. When just the ID1 unit is fluorescent, in the AU/ID1/ID2(NL)/TD (NL) system, energy transfer is 46%. This indicates that 30% of the transferred energy was coming from the ID2unit; which has its first donor group located 20 base pairs or 6.8 nm from the acceptor group. This is well beyond the Förster distance necessary to account for any significant level of energy transfer. When only the ID2 and TD units are fluorescent, in the (AU/ID1(NL)/ID2/TD) system, the energy transfer drops to about 8%. This is an important result, because it corroborates the other results showing that the ID2 and TD units were transferring through the ID1 unit to the AU unit. The AU/ID1(NL)/ID2(NL)/TD(NL) system result at 495 nm excitation simply shows the level of Texas Red background fluorescence for AU; and the result at 595 nm excitation gives the normal or base level of Texas Red fluorescence for AU.

The assembly, heating and cooling experiment clearly demonstrates the reversible organization properties of the system, by showing complete loss of energy transfer at 90° C. when the system is completely disassembled, and the return of energy transfer capability when the system is cooled.

2. Demonstration of Nonfluorescent Donor to Fluorescent Acceptor Energy Transfer With Significant Re-Emission Several oligonucleotides were designed and synthesized to demonstrate that certain nonfluorescent donor groups which energy transfer to Texas Red can lead to significant re-emission. The same basic procedures that were described in the Synthesis and Labeling Section and in Example 1 were used to synthesize and label two complementary 18-mer sequences. Oligonucleotide (A) below was functionalized (derivatized) with a primary amino group on the sixth nucleotide from its 3'-terminal position. Oligonucleotide (B) below was functionalized with a 5'-terminal amino group using the Aminolink 2 chemistry. Oligonucleotide (A) was then labeled with Fluorescein, DABITC (Molecular Probes), Reactive Red (Sigma Chemical), or Malachite Green (Molecular Probes). DABITC, Reactive Red 4, and Malachite Green are nonfluorescent chromophore groups. Oligonucleotide (B) was labeled with Texas Red. The oligonucleotide sequences are shown below and labeled as SEQ ID NOs 9–10, respectively:

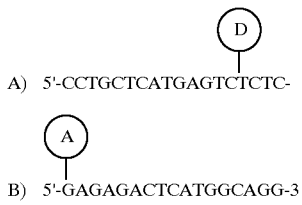

where D=Fluorescein, DABITC, Reactive Red 4 or Malachite Green, and A=Texas Red.

When hybridized together oligonucleotide (A) and (B) produce a 5 base pair spacing (2.0 nm) between the donor and acceptor groups. The hybridized arrangement for Texas Red (A) and Fluorescein (B) oligomers is shown below and labeled as SEQ ID NOs 9–10, respectively:

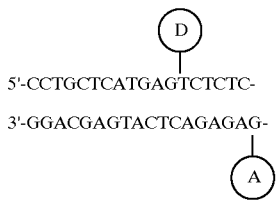

Oligonucleotides corresponding to oligonucleotide (A) but having one of fluorescein, DABITC, Reactive Red 4, or Malachite Green were independently tested to determine their respective energy transfer capacity to the Texas Red acceptor group on oligonucleotide (B). The structures were formed by combining the above oligonucleotides (A) and (B) at a concentration of 0.5 nanomole/μl in 500 μl of aqueous buffer (0.1M sodium chloride/0.02M sodium phosphate, pH 7.8) at 20° C. These conditions are optimal for the oligonucleotide units to quickly hybridize (one minute) to their complementary sequences. The fluorescent analysis experiments were carried out using the equipment and procedures as described in Example 1.

The following results were obtained:

(i) Fluorescein-labeled oligo (A) when hybridized to Texas Red-labeled (B) produced about 55% energy transfer as re-emission at 615 nm when the arrangement was excited at 495 nm (the fluorescein excitation maximum). This is reasonably good efficiency for this system. However, significant background fluorescence is still present from the donor group. That is, 45% of the fluorescent emission (~500 nm to ~600 nm) from fluorescein is still present.

(ii) DABITC-labeled oligo (A) when hybridized to Texas Red-labeled oligo (B) produced about 5% to 10% energy transfer as re-emission at 615 nm when the arrangement was excited at 430 nm (the DABITC excitation maximum). However, there was no detectable fluorescent emission form just beyond the excitation of DABITC at ~440 nm, to the beginning of the Texas Red fluorescent emission at ~600 nm. In this same arrangement DABITC appears to produce little or no quenching of the Texas Red fluorescent emission (615 nm), when the arrangement was excited at 595 nm (the Texas Red excitation maximum).

(iii) Reactive Red 4-labeled oligo (A) when hybridized to Texas Red-labeled oligo (B) produced no positive energy transfer as re-emission at 610 nm when the arrangement was excited at 535 nm (the Reactive Red 4 excitation maximum). Reactive Red 4 produced over 80% quenching of Texas Red fluorescent emission (615 nm) when the arrangement was excited at 595 nm (the Texas Red excitation maximum).

(iv) Malachite Green-labeled oligo (A) when hybridized to Texas Red-labeled oligo (B) produced over 60% quenching of Texas Red fluorescent emission (615 nm) when the arrangement was excited at 595 nm (the Texas Red excitation maximum). Malachite Green's excitation maximum is at 629 nm.

The results described above in (i) and (ii) clearly demonstrate that DABITC, a nonfluorescent chromophore group, at a 5 base pair spacing (2.0 nm) can produce significant fluorescent re-emission in a Texas Red acceptor. Also, DABITC produces no detectable background fluorescence in the same range where fluorescein produces significant background (45%). With regard to multiple donor systems, this is much more important than the fact that the re-emission produced by transfer from DABITC (5% to 10%) is lower than from fluorescein (55%). In a multiple donor system, the additive effect of background fluorescence from the fluorescent donors can very quickly limit its performance and usefulness. Thus, DABITC and similar chromophores are more ideal for use in multiple donor systems.

The result described above in (iii) and (iv) demonstrate that other non fluorescent chromophore groups (Reactive Red and Malachite Green) at a spacing of 5 base pairs (2.0 nm) can significantly quench the fluorescent emission of a Texas red acceptor. These strong quencher groups can be useful in devising mechanisms which would allow amplified photonic emissions to be switched on and off. Thus, they help to create a more novel and useful photonic mechanism or device. An example of a useful system in which a quencher group is utilized to reduce background is described in Example 4 and shown in FIG. 4.

3. A Homogeneous DNA Hybridization Assay Method Based On Extended Energy Transfer The following describes a homogeneous DNA hybridization assay method which utilizes a low fluorescent background extended energy transfer process. The system involves a multiple donor, an acceptor and a quencher oligonucleotide.

A multiple donor oligonucleotide (MDO) of 20 to 100 nucleotides in length is labeled with DABITC (nonfluorescent) donor groups at spacings of from 3 to 6 base pairs. The multiple donor system could also be an arrangement of a number of multiple donor probes, similar to the arrangement discussed in Example 1. A portion of at least 10 to 50 nucleotides of multiple donor oligomer is complementary to a specific portion of a target DNA sequence.

An acceptor oligonucleotide (AO) of 15 to 50 nucleotides in length, is labeled with Texas Red at or near its 5'-terminal position, and is complementary to that portion of the DNA target sequence continuous with the target sequence specific for the multiple donor oligomer.

A quencher oligonucleotide (QO) of 10 to 45 nucleotides in length, is labeled with Reactive Red 4 near its 3'-terminal position. The quencher oligomer is made complementary to the acceptor oligomer, but is 5 to 10 bases shorter. The Quencher oligomer is constructed so that when it is hybridized to the acceptor oligomer, the Reactive Red 4 group is within 1 to 5 bases of the Texas Red group, causing complete quenching of the Texas Red fluorescence.

Figure 4A:
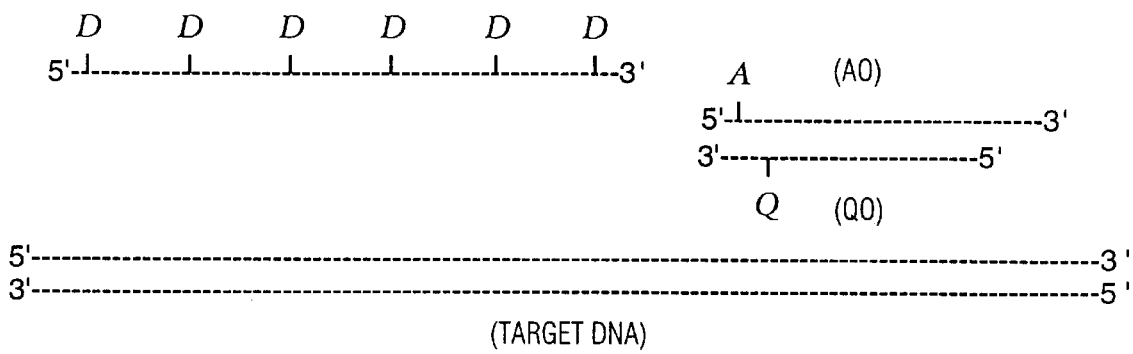
FIGS. 4A and 4B illustrate a homogeneous DNA hybridization assay method based on extended energy transfer as described in Example 3. The polynucleotides shown include the multiple donor-containing oligomer (MDO), the acceptor oligomer (AO), the quencher oligomer (QO) and a target DNA.
Figure 4B:
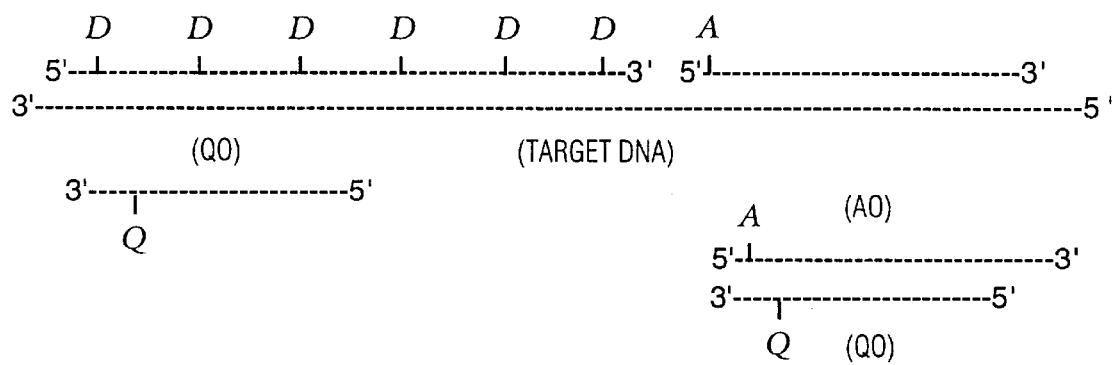

FIG. 4 shows the homogeneous assay procedure. This procedures can be carried using aqueous buffers common to the art of hybridization. Initially the multiple donor oligomer is provided into the homogeneous system as an unhybridized (single-stranded) oligomer and the quencher oligomer is provided to the system hybridized to the acceptor oligomer. The target DNA is either already present or now added to the assay system. The system is then heated to a temperature which causes denaturation of the target DNA. The system is then cooled to allow the new specific hybridizations to take place. The donor oligomer then hybridizes to its complementary sequence on the target DNA and the acceptor oligomer also hybridizes to the target DNA, adjacent to the multiple donor. Both oligomers are constructed relative to a preselected target sequence so that upon programmed assembly (hybridization) the terminal donor group is located within 3 to 6 base pairs of the acceptor group. The quencher oligomer is designed to be shorter in length than the acceptor and therefor cannot effectively compete with target sequences for hybridization to the target bound acceptor oligomer. Any unhybridized acceptor oligomer re-hybridizes with quencher oligomer. The target DNA has now organized the donor oligomer and the acceptor oligomer for efficient extended energy transfer to the Texas Red group. Target DNA can be quantitatively determined by fluorescent analysis.

The above assembled system is then excited at 430 nm and the fluorescent emission at 615 nm is determined. This homogeneous system has the unique advantages of having no fluorescent background from the any of the multiple donor groups as well as from any of the nontarget hybridized acceptor oligomer. This particular procedure represents just one of a number of possible homogeneous and heterogeneous DNA assay systems that can be developed based on novel extended energy transfer mechanisms.

4. Demonstration Of Efficient Energy Transfer In A Closely Approximated Donor-Acceptor Arrangement The following describes the demonstration of efficient energy transfer in an oligonucleotide in which the terminal acceptor (Texas Red) is separated by one nucleotide unit (0.34 nm) from its primary donor (Fluorescein). The arrangement of the fluorescein donor and Texas Red acceptor in the nucleotide sequence is shown below (SEQ ID NO 11):

5'-(TR)—G—(F)—GAGACTCATGAGCAGGGGCTAGC-3'

The above fluorescent modified oligonucleotide was made synthetically using the previously described techniques, except that a fluorescein (F) phosphoramidite (Clontech) replaced the second nucleotide in from the 5' terminus of the oligonucleotide. This second nucleotide position was functionalized with standard C6 linker amine (Aminolink 2), which was subsequently reacted with Texas Red. The resulting oligonucleotide derivative was purified by polyacrylamide gel (15%) electrophoresis.

Fluorescent energy transfer for this fluorescent phosphoramidite derivative oligonucleotide was carried out after first hybridizing the derivative to a complementary oligonucleotide. The concentration for both the oligonucleotides was 25 μg/ml; and hybridization was carried out at room temperature in 1× SSC (pH 7.0). When excited at 490 nm, this derivative produced >50% energy transfer, in terms of 610 nm re-emission by the Texas Red acceptor. This clearly demonstrates a closely spaced donor-acceptor arrangement in which secondary quenching mechanisms have been reduced, and higher energy transfer in terms of acceptor re-emission is observed.

The foregoing is intended as illustrative of the present invention but not limiting. Numerous variations and modifications can be effected without departing from the true spirit and scope of the invention.

What is claimed is:

1. A biosensor for detecting the presence of an analyte in solution, said analyte comprising a target DNA sequence, said biosensor comprising:
   an excitation source for delivering emitting photonic energy;
   a donor sequence comprising a first polynucleotide having a terminal donor chromophore and at least one intermediate donor chromophore linked to said first polynucleotide by linker arms, wherein said first polynucleotide is complementary to a first region of said target DNA sequence;
   an acceptor sequence comprising a second polynucleotide having at least one acceptor chromophore linked to said second polynucleotide by linker arms, wherein said second polynucleotide is complementary to a second region of said target DNA sequence; and
   an associated photon sensing means to detect photonic energy emitted from said acceptor;
   wherein said first polynucleotide and said second polynucleotide are able to hybridize with said target DNA sequence to form a complex wherein the distance between said terminal donor chromophore and one said acceptor chromophore is greater than 5 nm and there is at least one said intermediate donor chromophore.

2. The biosensor of claim 1, wherein said analyte, upon hybridization, is associated in close proximity to said photon sensing means.

3. The biosensor of claim 1, wherein at least one of said first polynucleotide, said second polynucleotide, and said target DNA sequence is bound to a solid support or matrix that is insoluble in the analyte solution.

4. The biosensor of claim 3, wherein said solid support or matrix is selected from the group consisting of glass, metals, silicon, organic polymers, membranes, and bio-polymers.

5. The biosensor of claim 1, wherein said associated photon sensor means is selected from the group consisting of a photodiode, photodiode array, photomultiplier tube, and a fiber optic detection system.

6. An electronic device comprising:
   an extended energy transfer system comprising a polynucleotide having a terminal donor chromophore, at least one intermediate donor chromophore, and at least one acceptor chromophore linked to said polynucleotide by linker arms, wherein the distance between said terminal donor chromophore and one said acceptor chromophore is greater than 5 nm and there is at least one said intermediate donor chromophore; and
   wherein said polynucleotide is linked to a solid support.

7. The electronic device of claim 6, wherein the solid support is selected from the group consisting of glass, metals, silicon, organic polymers, membranes, and biopolymers.

8. The electronic device of claim 6, wherein said device is a photonic energy collector.

9. The electronic device of claim 6, wherein said device is a light amplifier.

10. The electronic device of claim 6, wherein said device is an energy transfer conduit.

11. The electronic device of claim 6, wherein the solid support is adapted to provide a complementary function.

12. The electronic device of claim 11, wherein the function is to donate energy to the extended energy transfer system.

13. The electronic device of claim 11, wherein the function is to detect emitted photonic energy.

14. The electronic device of claim 11, wherein the function is to receive emitted photonic energy.

15. The electronic device of claim 11, wherein the function is to convert emitted photonic energy.

16. The electronic device of claim 11, wherein the function is to transmit emitted photonic energy to a second circuit.

17. The electronic device of claim 11, wherein the function is to translate emitted photonic energy.

18. The electronic device of claim 16, wherein the second circuit is a photosensor.

19. The electronic device of claim 16, wherein the second circuit is a photovoltaic cell.

20. An extended photonic energy transfer system able to communicate with an electronic circuit, said transfer system comprising:
   a polynucleotide having a terminal donor chromophore, at least one intermediate donor chromophore, and at least one acceptor chromophore linked to said polynucleotide by linker arms;
   wherein the distance between said terminal donor chromophore and one said acceptor chromophore is greater than 5 nm and there is at least one said intermediate donor chromophore; and
   wherein at least one said chromophore is adapted to convert electronic energy to photonic energy.

21. The transfer system of claim 20, wherein the chromophore adapted to convert electronic energy to photonic energy is selected from the group consisting of luminescent compounds, ruthenium complexes, and photovoltaic cells.

22. An extended photonic energy transfer system able to communicate with an electronic circuit, said transfer system comprising:
   a polynucleotide having a terminal donor chromophore, at least one intermediate donor chromophore, and at least one acceptor chromophore linked to said polynucleotide by linker arms;
   wherein the distance between said terminal donor chromophore and one said acceptor chromophore is greater than 5 nm and there is at least one said intermediate donor chromophore; and
   wherein at least one said chromophore is adapted to convert photonic energy to electronic energy.

23. The transfer system of claim 22, wherein the chromophore adapted to convert photonic energy to electronic energy is selected from the group consisting of luminescent compounds, ruthenium complexes, and photovoltaic cells.

* * * * *

UNITED STATES PATENT AND TRADEMARK OFFICE
CERTIFICATE OF CORRECTION

| | | |
|---|---|---|
| PATENT NO. : | 5,849,489 | Page 1 of 2 |
| DATED : | December 15, 1998 | |
| INVENTOR(S) : | Heller | |

It is certified that error appears in the above-identified patent and that said Letters Patent is hereby corrected as shown below:

On the title page item [56], under OTHER PUBLICATIONS:

Column 2, line 8, insert -- -- (a space) between ", " and "Stockton".

Column 2, line 14, delete "probes" and insert --Probes--.

Column 6, line 34, delete "wit" and insert --with--.

Column 6, line 67, delete "F".

Column 7, line 1, delete "örster" and insert --Förster--.

Column 8, line 28, delete "express" and insert --expresses--.

Column 11, line 61, insert --,-- between "2" and "a".

Column 14, line 1, delete "case" and insert --cases--.

Column 19, line 54, delete "polypeptide" and insert --polynucleotide--.

Column 21, line 39, delete "ug/ml" and insert --ng/ml--.

Column 22, line 44, delete "," between "nm" and "(RD)".

UNITED STATES PATENT AND TRADEMARK OFFICE
CERTIFICATE OF CORRECTION

PATENT NO. : 5,849.489
DATED : December 15, 1998
INVENTOR(S) : Heller

It is certified that error appears in the above-identified patent and that said Letters Patent is hereby corrected as shown below:

Column 22, line 66, insert --'-- after "-3".

Column 25, line 12, delete "AU/ID1/ID2(ND/TD (NL)" and insert

--AU/ID1/ID2(NL)/TD(NL)--.

Column 25, line 31, delete "ID2unit" and insert --ID2 unit--.

Column 25, line 33-34, delete "F örster" and insert --Förster--.

Column 27, line 64, delete "Quencher" and insert --quencher--.

Column 28, line 1, delete "This" and insert --These--.

Signed and Sealed this

Seventeenth Day of August, 1999

Attest:

Attesting Officer

Q. TODD DICKINSON

Acting Commissioner of Patents and Trademarks

UNITED STATES PATENT AND TRADEMARK OFFICE
CERTIFICATE OF CORRECTION

PATENT NO. : 5,849,489
DATED : December 15, 1998
INVENTOR(S) : Heller

It is certified that error appears in the above-identified patent and that said Letters Patent is hereby corrected as shown below:

Title page,
Item [56], References Cited, OTHER PUBLICATIONS, "Keller et al.," reference, insert -- -- (a space) between "," and "Stockton".
"Glazer et al.," reference, delete "probes" and insert -- Probes --.
Item [63], delete "Continuation of Ser. No. 232,233, filed as PCT/US92/09827 Nov. 6, 1992, Pat No. 5,565,322," and insert -- Continuation of U.S. application Ser. No. 08/232,233, filed on May 5, 1994, now U.S. Pat. No. 5,565,322, which was filed under 35 U.S.C. § 371 based on International Application PCT/US92/09287, filed Nov. 6, 1992 --; delete "Ser. No. 250,951, May 27, 1994, Pat. No. 5,532,129, which is a continuation of"

Column 1,
Line 12, delete "U.S. Application Ser. No. 250,951, filed May 27, 1994, now U.S. Pat. No. 5,532,129, which is a continuation of"

Column 6,
Line 34, delete "wit" and insert -- with --.
Line 67, delete "F".

Column 7,
Line 1, delete "örster" and insert -- Förster --.

Column 8,
Liune 28, delete "express" and insert -- expresses --.

Column 11,
Line 61, insert -- , -- between "2" and "a".

Column 14,
Line 1, delete "case" and insert -- cases --.

Column 16,
Line 47, delete "involve" and insert -- involves --.

Column 19,
Line 54, delete "polypeptide" and insert -- polynucleotide --.

UNITED STATES PATENT AND TRADEMARK OFFICE
CERTIFICATE OF CORRECTION

PATENT NO. : 5,849,489
DATED : December 15, 1998
INVENTOR(S) : Heller

It is certified that error appears in the above-identified patent and that said Letters Patent is hereby corrected as shown below:

Column 21,
Line 39, delete "ug/ml" and insert -- ng/ml --.

Column 22,
Line 44, delete "," between "nm" and "(RD)".
Line 66, insert -- ' -- after "-3".

Column 25,
Lien 12, delete "AU/ID1/ID2(ND/TD (NL)" and insert -- AU/ID1/ID2(NL)/TD(NL) --.

Column 25,
Line 31, delete "ID2unit" and insert -- ID2 unit --.
Lines 33-34, delete "F örster" and insert -- Förster --.

Column 27,
Line 64, delete "Quencher" and insert -- quencher --.

Column 28,
Line 1, delete "This" and insert -- These --.

Signed and Sealed this

Twenty-fourth Day of August, 2004

JON W. DUDAS
*Director of the United States Patent and Trademark Office*

SEQUENCE LISTING ( 1 ) GENERAL INFORMATION:

( i i i ) NUMBER OF SEQUENCES: 11

( 2 ) INFORMATION FOR SEQ ID NO: 1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: misc_feature
        ( B ) LOCATION: 10
        ( D ) OTHER INFORMATION: /note-"Donor chromphore at the 3'T nucleotide"

( x i ) SEQUENCE DESCRIPTION: SEQ ID NO: 1:

A T G C A T A C G T         1 0

( 2 ) INFORMATION FOR SEQ ID NO: 2:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: misc_feature
        ( B ) LOCATION: 1
        ( D ) OTHER INFORMATION: /note-"Acceptor chromphore at the 5'T nucleotide"

( x i ) SEQUENCE DESCRIPTION: SEQ ID NO: 2:

T C A G T A C G A T         1 0

( 2 ) INFORMATION FOR SEQ ID NO: 3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO: 3:

A T C G T A C T G A  A C G T A T G C A T         2 0

( 2 ) INFORMATION FOR SEQ ID NO: 4:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: misc_feature
        ( B ) LOCATION: 6
        ( D ) OTHER INFORMATION: /note-"Sulforhodamine 101 (Texas Red)- labelled T nucleotide"

( x i ) SEQUENCE DESCRIPTION: SEQ ID NO: 4:

ATGTCTGACT GCAGCT                                        16

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: misc_feature
        ( B ) LOCATION: 11
        ( D ) OTHER INFORMATION: /note-"Fluorescein-labelled T nucleotide"

( i x ) FEATURE:
        ( A ) NAME/KEY: misc_feature
        ( B ) LOCATION: 18
        ( C ) OTHER INFORMATION: /note-"Fluorescein-labelled T nucleotide"

( x i ) SEQUENCE DESCRIPTION: SEQ ID NO: 5:

ACGACCATAG TGCGAGCTGC AGTCAGACAT                        30

( 2 ) INFORMATION FOR SEQ ID NO: 6:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: misc_feature
        ( B ) LOCATION: 11
        ( D ) OTHER INFORMATION: /note-"Fluorescein-labelled T nucleotide"

( i x ) FEATURE:
        ( A ) NAME/KEY: misc-feature
        ( B ) LOCATION: 18
        ( D ) OTHER INFORMATION: /note-"Fluorescein-labelled T nucleotide"

( x i ) SEQUENCE DESCRIPTION: SEQ ID NO: 6:

CGCACTATGG TCGTGAGTGT TGAGAGGCT 29

( 2 ) INFORMATION FOR SEQ ID NO: 7:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: misc_feature
        ( B ) LOCATION: 11
        ( D ) OTHER INFORMATION: /note-"Fluorescein-labelled T nucleotide"

( i x ) FEATURE:
        ( A ) NAME/KEY: misc_feature
        ( B ) LOCATION: 19
        ( D ) OTHER INFORMATION: /note-"Fluorescein-labelled T nucleotide"

( x i ) SEQUENCE DESCRIPTION: SEQ ID NO: 7:

ACGACCATAG TGCGAGCCTC TGAACACTC 29

( 2 ) INFORMATION FOR SEQ ID NO: 8:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: misc_feature
        ( B ) LOCATION: 5
        ( D ) OTHER INFORMATION: /note-"Fluorescein-labelled T nucleotide"

( x i ) SEQUENCE DESCRIPTION: SEQ ID NO: 8:

AGCCTCTGAA CACTC 15

( 2 ) INFORMATION FOR SEQ ID NO: 9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: misc_feature
        ( B ) LOCATION: 13

-continued (D) OTHER INFORMATION: /note-"Fluorescein-labelled T
    nucleotide"

(x i) SEQUENCE DESCRIPTION: SEQ ID NO: 9:

CCTGCTCATG AGTCTCTC                                                                                  18

(2) INFORMATION FOR SEQ ID NO: 10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (i x) FEATURE:
        (A) NAME/KEY: misc_feature
        (B) LOCATION: 1
        (D) OTHER INFORMATION: /note-"Texas Red-labelled G
            nucleotide"

(x i) SEQUENCE DESCRIPTION: SEQ ID NO: 10:

GAGAGACTCA TGAGCAGG                                                                                  18

(2) INFORMATION FOR SEQ ID NO: 11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (i x) FEATURE:
        (A) NAME/KEY: misc_feature
        (B) LOCATION: 1
        (D) OTHER INFORMATION: /note-"The 5'G nucleotide
            separates the terminal Texas Red (TR) acceptor from
            its primary donor, fluorescein (F)"

(x i) SEQUENCE DESCRIPTION: SEQ ID NO: 11:

GGAGACTCAT GAGCAGGGGC TAGC                                                                           24